United States Patent
Sato

(10) Patent No.: US 8,320,998 B2
(45) Date of Patent: Nov. 27, 2012

(54) VEIN IMAGING APPARATUS, POSITIONAL DISPLACEMENT INTERPOLATION METHOD, AND PROGRAM

(75) Inventor: Hideo Sato, Tokyo (JP)

(73) Assignee: Sony Corporation, Tokyo (JP)

( * ) Notice: Subject to any disclaimer, the term of this patent is extended or adjusted under 35 U.S.C. 154(b) by 168 days.

(21) Appl. No.: 12/775,211

(22) Filed: May 6, 2010

(65) Prior Publication Data

US 2010/0292578 A1 Nov. 18, 2010

(30) Foreign Application Priority Data

May 14, 2009 (JP) ................ P2009-117985

(51) Int. Cl.
*A61B 6/00* (2006.01)
(52) U.S. Cl. ........ 600/474; 600/160; 600/476; 600/478; 600/473; 382/128; 382/130; 382/131
(58) Field of Classification Search .......... 382/128, 382/130, 131; 600/160, 476, 478, 473, 474
See application file for complete search history.

(56) References Cited

U.S. PATENT DOCUMENTS

| 6,485,413 | B1 * | 11/2002 | Boppart et al. ........ 600/160 |
| 7,415,139 | B2 * | 8/2008 | Takiguchi ........ 382/115 |
| 7,869,624 | B2 * | 1/2011 | Takiguchi ........ 382/115 |
| 2005/0180620 | A1 * | 8/2005 | Takiguchi ........ 382/128 |
| 2007/0003112 | A1 * | 1/2007 | Awatsu et al. ........ 382/115 |
| 2007/0116330 | A1 * | 5/2007 | Takiguchi ........ 382/115 |
| 2008/0118114 | A1 * | 5/2008 | Takiguchi ........ 382/124 |
| 2008/0205711 | A1 * | 8/2008 | Kishigami et al. ........ 382/115 |
| 2011/0001814 | A1 * | 1/2011 | Yamanaka et al. ........ 348/78 |

FOREIGN PATENT DOCUMENTS

JP 2004-296531 10/2004

* cited by examiner

*Primary Examiner* — Tse Chen
*Assistant Examiner* — Baisakhi Roy
(74) *Attorney, Agent, or Firm* — Finnegan, Henderson, Farabow, Garrett & Dunner, L.L.P.

(57) ABSTRACT

An imaging element of a vein imaging apparatus includes a vein image data generation region generating image data of a vein based a near-infrared light that was condensed by a lens array and that was scattered in a living body and transmitted through the vein and a positional displacement detection data generation region that includes a shielded section in which pixels are shielded from the light and an opening section in which pixels are not shielded from the light, and generates data for detecting positional displacement that is used to detect, based on the light received via the opening section, variation in an image focus position according to an imaging temperature. The vein imaging apparatus detects the image focus position of the light and estimates the amount of positional displacement occurred in the apparatus. The vein imaging apparatus selects a pixel based on the obtained amount of positional displacement.

19 Claims, 13 Drawing Sheets

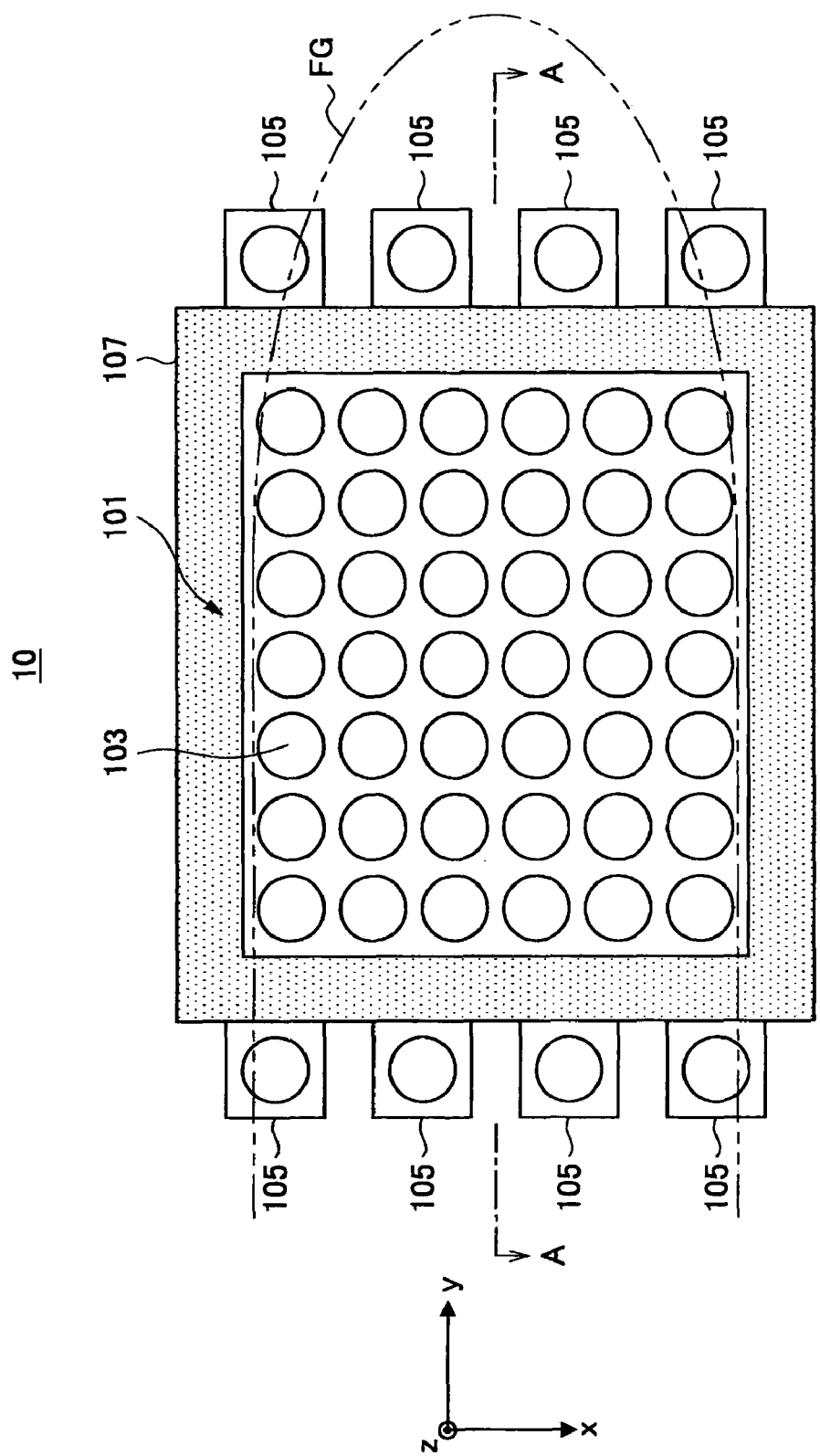

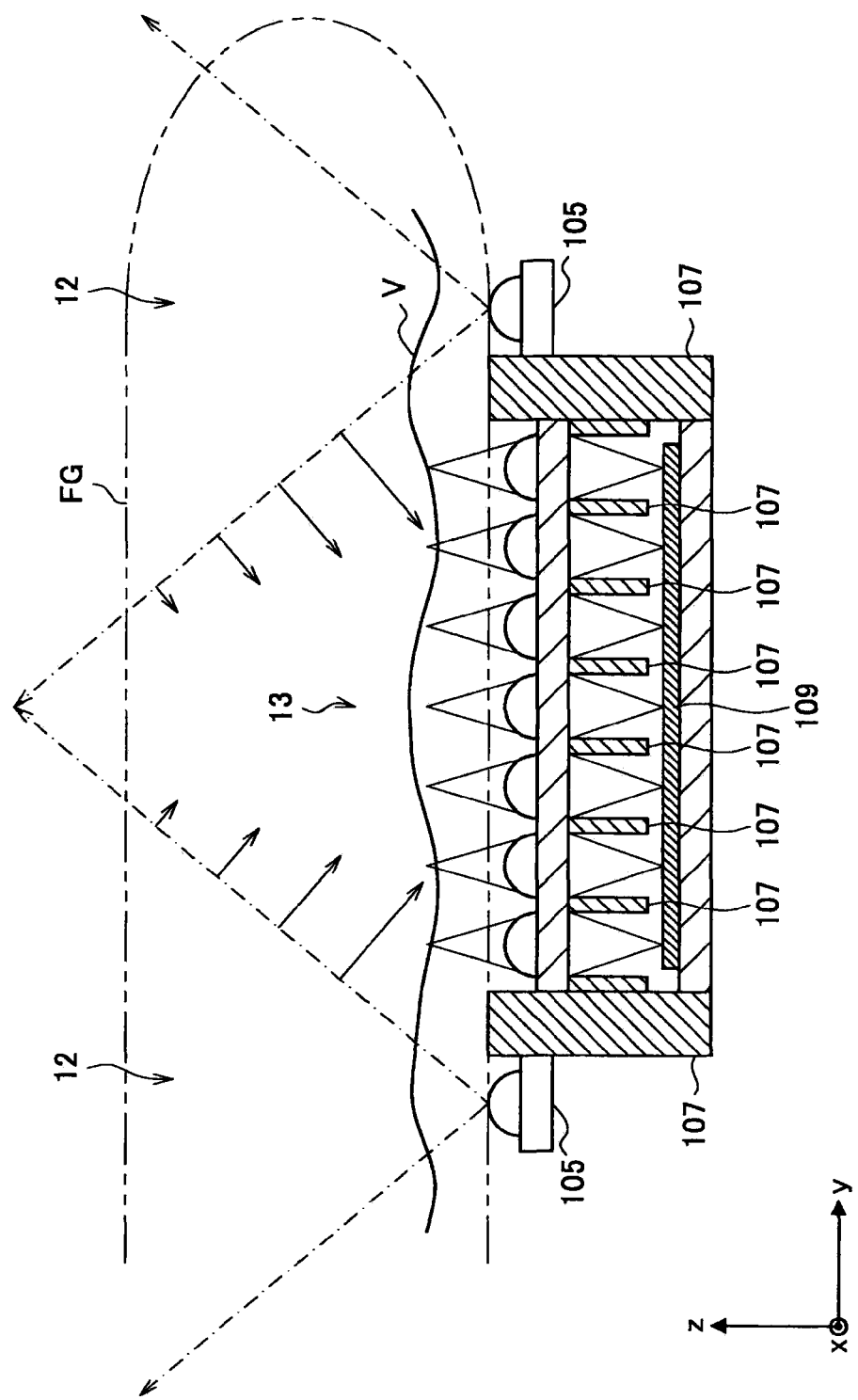

POSITIONAL DISPLACEMENT DETECTION DATA GENERATION REGION

VEIN IMAGE DATA GENERATION REGION

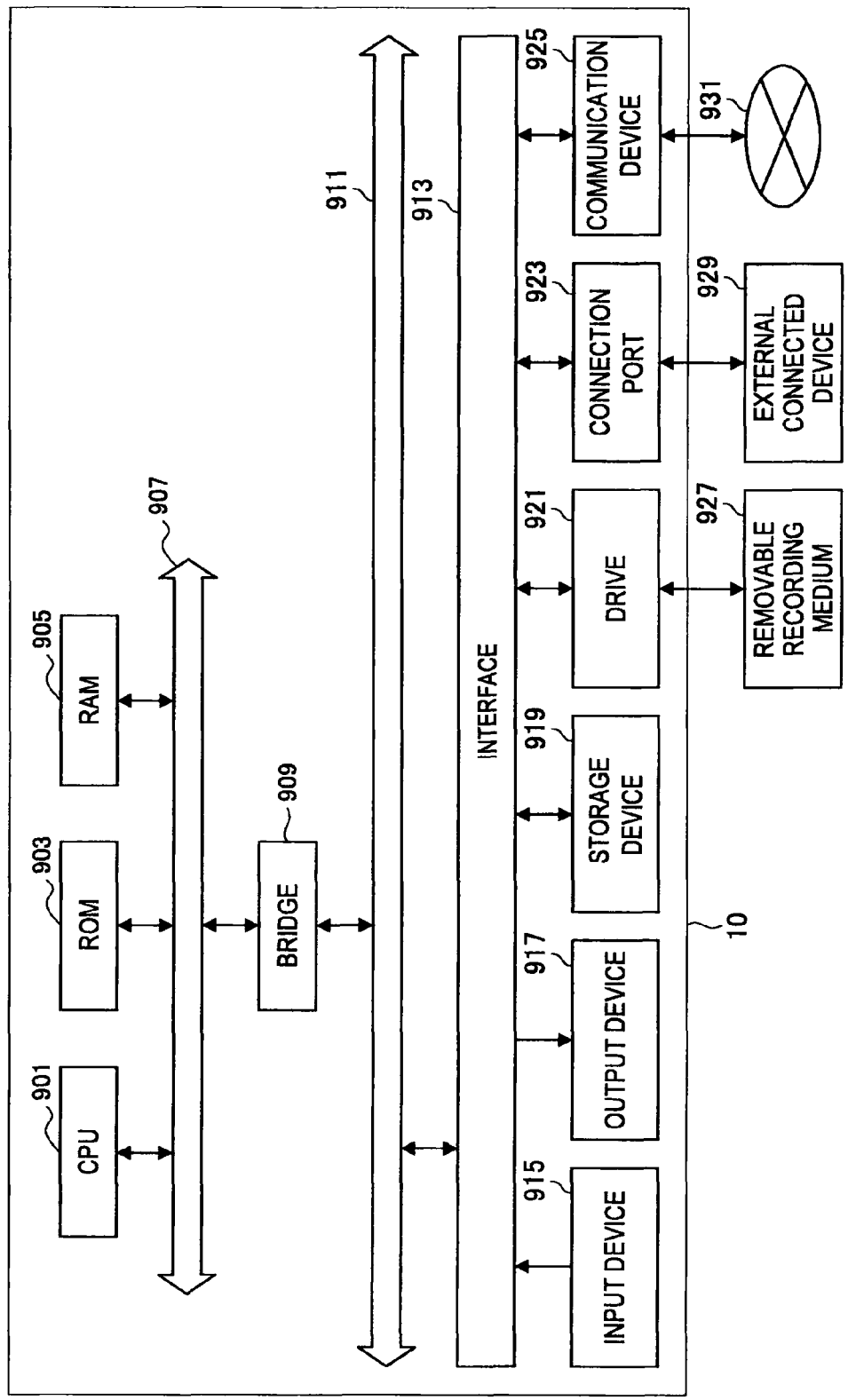

VEIN IMAGING APPARATUS, POSITIONAL DISPLACEMENT INTERPOLATION METHOD, AND PROGRAM

BACKGROUND OF THE INVENTION

1. Field of the Invention

The present invention relates to a vein imaging apparatus, a positional displacement interpolation method, and a program.

2. Description of the Related Art

Biometric individual authentication is highly important technology for protecting the rights in the future network society. In commercial transactions conducted on the Internet in which money, contents, and rights can be stolen any time over the network by means of spoofing, biometric individual authentications particularly attract attention as a technique for protecting a field that may not be protected by encryption alone. However, a biometric individual authentication using fingerprint and iris may not solve the issue of counterfeiting. With regard to this issue, an individual authentication technique using a part of the vein pattern that may not be easily imaged from the outside is expected to be a biometric individual authentication for the next generation because of accuracy of determination and difficulty for counterfeiting and spoofing.

On the other hand, in developing an imaging method for taking a vein image, it is difficult to produce an imaging device with a planar structure because the position of a light source is strictly restricted. In order to solve this issue, there has been suggested a method using a wide-angle lens and the like. However, even with this method, it is difficult to limit the distance between a finger and the imaging device, and the user is required to surely place the finger at the same distance. Therefore, the reproducibility of the authentication may not be ensured. A contact or non-contact device with a large sensor is ideal in principle, but the large sensor size results in increasing the cost due to expensive optical materials. In addition, in some types of optical components for the large sensor, there is also an issue of displacement of the arrangement between the optical components and the large sensor due to thermal expansion.

In order to solve the positional displacement caused by thermal expansion among the above-described issues, for example, Japanese Patent Application Laid-Open No. 2004-296531 describes a technique for detecting the amount of positional displacement caused by thermal expansion and directly controlling the position of an optical component based on the amount of positional displacement.

SUMMARY OF THE INVENTION

However, when the method described in Japanese Patent Application Laid-Open No. 2004-296531 is applied to a vein imaging apparatus having a planar structure, a new positional adjustment member is required in order to adjust the position of the optical component. As a result, when the technique described in Japanese Patent Application Laid-Open No. 2004-296531 is implemented in a mobile device and the like whose range of operational environment temperature is wide, there is an issue that it is difficult to produce the device smaller.

In light of the foregoing, it is desirable to provide a vein imaging apparatus, a positional displacement interpolation method, and a program that make it possible to correct a positional displacement between an imaging element and an optical component caused by thermal expansion and to produce the apparatus smaller.

According to an embodiment of the present invention, there is provided a vein imaging apparatus including a lens array including a plurality of light-receiving lenses disposed in an array, a near-infrared light emission source which is arranged at an end of the lens array and emits a near-infrared light to a part of a living body, an imaging element including a vein image data generation region for generating image data of a vein based on the near-infrared light that was condensed by the lens array and that was scattered in the living body and transmitted through the vein, and a positional displacement detection data generation region that includes a shielded section in which pixels are shielded from the light and an opening section in which pixels are not shielded from the light, and generates data for detecting a positional displacement that is used to detect, based on the light received via the opening section, variation in an image focus position according to an imaging temperature, where a plurality of pixels are assigned to one of the light-receiving lenses, an image focus position detection unit for detecting a image focus position at imaging temperature based on the data for detecting positional displacement obtained from the positional displacement detection data generation region, a positional displacement amount estimation unit for estimating an amount of displacement of the image focus position at the imaging temperature based on the image focus position detected by the image focus position detection unit, and a pixel selection unit for selecting based on the amount of displacement, a pixel generating the vein image data used to generate vein image from among the plurality of pixels corresponding to one of the light-receiving lenses.

According to the above configuration, the image focus position detection unit detects the image focus position at the imaging temperature based on the data for detecting positional displacement obtained from the positional displacement detection amount data generation region of the imaging element. Further, the positional displacement amount estimation unit estimates the amount of displacement of the image focus position at the imaging temperature based on the image focus position detected by the image focus position detection unit. Further, the pixel selection unit selects based on the amount of displacement, a pixel for generating the vein image data used to generate the vein image from among the plurality of pixels corresponding to one of the light-receiving lenses.

The vein imaging apparatus preferably further includes a drive control unit for performing drive control of at least one of the near-infrared light emission source and the imaging element. The drive control unit preferably performs drive control of the near-infrared light emission source and/or the imaging element based on the amount of displacement transmitted from the positional displacement amount estimation unit.

The vein imaging apparatus may further include a vein pattern extraction unit that extracts a vein pattern from the vein image generated using the vein image data, and a vein image interpolation unit that performs interpolation processing on the vein image, from which the vein pattern is extracted, based on the amount of displacement estimated by the positional displacement amount estimation unit.

The vein image interpolation unit may perform interpolation processing on the vein image by using the vein image data obtained from the pixels, located around a reference unit region serving as a reference unit for pixel selection by the pixel selection unit, from among the plurality of pixels corresponding to one of the light-receiving lenses.

The pixel selection unit may select a pixel included in a region in which the sum of the light quantity detected by the pixel is the largest from among the plurality of pixels corresponding to one of the light-receiving lenses.

The vein imaging apparatus may further include a temperature estimation unit for estimating the imaging temperature based on the amount of displacement obtained from the positional displacement amount estimation unit.

The vein imaging apparatus may further include a warning unit that gives a warning when the amount of displacement output from the positional displacement amount estimation unit or the imaging temperature output from the temperature estimation unit is equal to or more than a predetermined threshold value.

According to another embodiment of the present invention, there is provided a positional displacement interpolation method including the steps of detecting a image focus position at imaging temperature based on data for detecting positional displacement obtained from a positional displacement detection data generation region of a vein imaging apparatus including a lens array including a plurality of light-receiving lenses disposed in an array, a near-infrared light emission source which is arranged at an end of the lens array and emits a near-infrared light to a part of a living body, and an imaging element including a vein image data generation region for generating image data of a vein based on the near-infrared light that was condensed by the lens array and that was scattered in the living body and transmitted through the vein, and the positional displacement detection data generation region that includes a shielded section in which pixels are shielded from the light and an opening section in which pixels are not shielded from the light, and generates data for detecting a positional displacement that is used to detect, based on the light received via the opening section, variation in an image focus position according to an imaging temperature, where a plurality of pixels are assigned to one of the light-receiving lenses, estimating an amount of displacement of the image focus position at the imaging temperature based on the detected image focus position, and selecting, based on the amount of displacement, a pixel generating the vein image data used to generate vein image from among the plurality of pixels corresponding to one of the light-receiving lenses.

According to another embodiment of the present invention, there is provided a program for causing a computer that controls a vein imaging apparatus to realize an image focus position detection function for detecting a image focus position at imaging temperature based on data for detecting positional displacement obtained from a positional displacement detection data generation region, a positional displacement amount estimation function for estimating an amount of displacement of the image focus position at the imaging temperature based on the image focus position detected by the image focus position detection function, and a pixel selection function for selecting, based on the amount of displacement, a pixel for generating vein image data used to generate vein image from among a plurality of pixels corresponding to one of light-receiving lenses, where the vein imaging apparatus includes a lens array including a plurality of light-receiving lenses disposed in an array, a near-infrared light emission source which is arranged at an end of the lens array and emits a near-infrared light to a part of a living body, and an imaging element including a vein image data generation region for generating image data of a vein based on the near-infrared light that was condensed by the lens array and that was scattered in the living body and transmitted through the vein, and the positional displacement detection data generation region that includes a shielded section in which pixels are shielded from the light and an opening section in which pixels are not shielded from the light, and generates data for detecting a positional displacement that is used to detect, based on the light received via the opening section, variation in an image focus position according to an imaging temperature, where a plurality of pixels are assigned to one of the light-receiving lenses.

As described above, according to the embodiments of the present invention, a positional displacement can be corrected between an imaging element and an optical component caused by thermal expansion, and the apparatus can be produced smaller.

BRIEF DESCRIPTION OF THE DRAWINGS

FIG. 2 is an explanatory diagram for illustrating a vein imaging apparatus according to the embodiment;

FIG. 3 is an explanatory diagram for illustrating a vein imaging apparatus according to the embodiment;

FIG. 13 is a block diagram for illustrating a hardware configuration of a vein imaging apparatus according to each embodiment of the present invention.

DETAILED DESCRIPTION OF THE EMBODIMENT(S)

Figure 1:
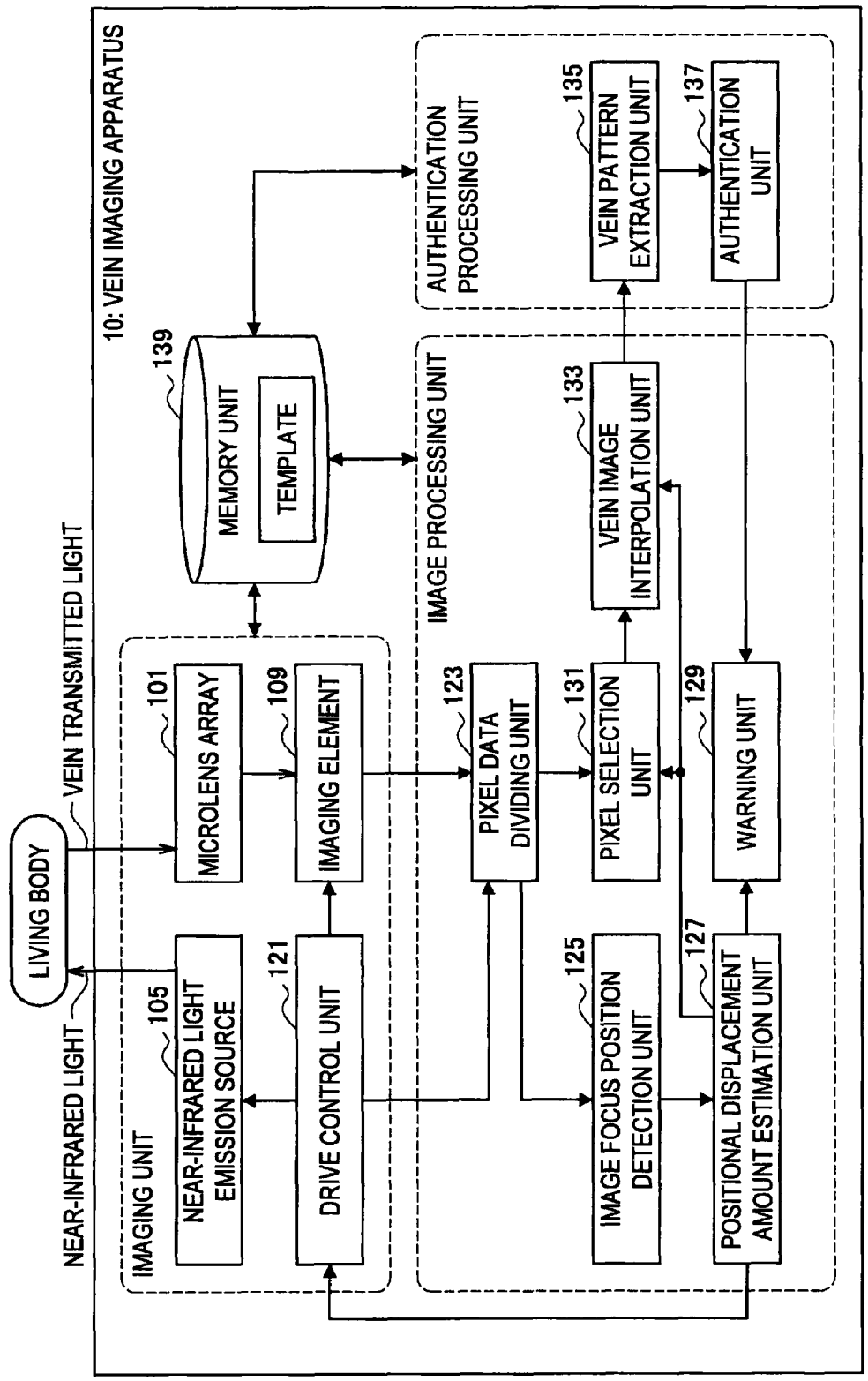
FIG. 1 is a block diagram for illustrating a configuration of a vein imaging apparatus according to a first embodiment of the present invention.

Hereinafter, preferred embodiments of the present invention will be described in detail with reference to the appended drawings. Note that, in this specification and the appended drawings, structural elements that have substantially the same function and structure are denoted with the same reference numerals, and repeated explanation of these structural elements is omitted.

The description will be given in the following order.
(1) Object
(2) First embodiment
(1-1) Regarding configuration of vein imaging apparatus
Regarding configuration of imaging unit
Regarding an example of structure of imaging unit
Regarding image obtained by microlens array
Regarding imaging element
Regarding configuration of image processing unit
Regarding configuration of authentication processing unit
Regarding Obtaining data from particular pixel
(1-2) Regarding positional displacement interpolation method
(2) Second embodiment
(2-1) Regarding configuration of vein imaging apparatus
(3) Regarding hardware configuration of vein imaging apparatus according to each embodiment of the present invention
(4) Summary <Object>

Before describing a vein imaging apparatus and a positional displacement interpolation method according to each embodiment of the present invention, an object of the present invention will be first described with an explanation of the overview of the vein imaging apparatus.

In biometric authentication, especially in vein authentication, a method using a camera using as imaging element a Charge Coupled Device (CCD), a Complementary Metal Oxide Semiconductor (CMOS), and the like has been mainly used. Such vein authentication apparatus, however, has a larger body than that for a finger authentication, and accordingly, is applied to a limited range of applications.

In view of this circumstance, in the below-described vein imaging apparatus according to each embodiment of the present invention, a microlens array (MLA), i.e., a type of lens array and large sensor are used, which allows the vein imaging apparatus to be produced thinner.

An object of each embodiment of the present invention is to realize an automatic correction of deterioration caused by an environmental temperature and decreased imaging performance that may be caused by the environmental temperature, mechanical precision, and displacement, which are the issues of the vein imaging apparatus using a flat, large sensor device such as MLA and TFT.

A microlens array is a device suitable for reading a vein pattern located several millimeters below the skin. For example, a microlens arranged on the microlens array may be a lens for reducing the position of an object, a vein, by one half. In this case, the size of an image focused by the microlens is one-half the actual size. Therefore, when, for example, one microlens corresponds to eight-by-eight pixels, only with four-by-four pixels in the center of the eight-by-eight pixels, the combined image of the MLA is obtained.

When this image focus position is displaced, a fixed pixel selection method used in related art has issues of deterioration in the image quality and the like because there occur discontinuity and distortion at a boundary of a microlens. For example, when the temperature increases to 70 degrees Celsius, a microlens array formed with a plastic resin is known to have a displacement of one pixel or more, which may cause an issue that taken images may be the greatly deteriorated and an authentication may be performed erroneously unless any measure is taken.

In view of this issue, the below-described vein imaging apparatus according to each embodiment of the present invention aims to automate a correction by means of image processing and optimum sampling of each member at each temperature, by using pixels surrounding an imaging region of the imaging element for detection of displacement between members.

(First Embodiment)
<Regarding Configuration of Vein Imaging Apparatus>

First, the configuration of the vein imaging apparatus according to the first embodiment of the present invention will be described in detail with reference to FIG. 1 to FIG. 3. FIG. 1 is a block diagram for illustrating the configuration of the vein imaging apparatus according to the present embodiment. FIG. 2 is a plan view of the vein imaging apparatus according to the present embodiment. FIG. 3 is a cross sectional diagram taken along line A-A of FIG. 2.

As shown in FIG. 1, the vein imaging apparatus 10 according to the present embodiment includes, for example, three units, i.e., an imaging unit, an image processing unit, and an authentication processing unit, and further includes a storage unit 139.

The imaging unit performs processing of imaging a part of a living body (for example, a finger). As shown in FIG. 1, this imaging unit mainly includes, for example, a microlens array 101, a near-infrared light emission source 105, an imaging element 109, and a drive control unit 121.

The image processing unit performs processing when obtaining picture data (image data) related to a vein that is generated by the imaging unit, and performs various image processings on the obtained image data, and thus generates image (vein image) of veins which are in the inside of the living body. As shown in FIG. 1, this image processing unit mainly includes, for example, a pixel data dividing unit 123, a image focus position detection unit 125, a positional displacement estimation unit 127, a warning unit 129, a pixel selection unit 131, and a vein image interpolation unit 133.

The authentication processing unit performs authentication processing of the vein image generated by the image processing unit. As shown in FIG. 1, this authentication processing unit mainly includes, for example, a vein pattern extraction unit 135 and an authentication unit 137.

[Regarding Configuration of Imaging Unit]

First, the configuration of imaging unit will be hereinafter described in detail.

The microlens array (MLA) 101 condenses near-infrared light, which was emitted from the later-described near-infrared light emission source 105 to a part of a living body and transmitted through a vein inside the living body (which is also referred to hereinafter as vein transmitted light), onto the later-described imaging element 109. This microlens array 101 includes a plurality of light-receiving lens as described later. The microlens array 101 is made of, for example, a material that is more likely to be affected by heat than glass material. By using such material, it becomes possible to inexpensively bulk-produce microlens array of any size by means of, for example, molding. An example of such material that is more likely to be affected by heat than glass material includes a plastic resin.

The near-infrared light emission source 105 emits near-infrared light having a predetermined wavelength band onto a part of a living body placed on the vein imaging apparatus 10. Because the near-infrared light has characteristics that it is well transmitted through body tissues and absorbed by hemoglobin (reduced hemoglobin) in blood, if the near-infrared light is emitted on the finger, palm or back of a hand, veins distributed inside the finger, palm or back of the hand appear as a shadow in an image. The shadow of veins that appears in an image is called a vein pattern. In order to suitably image such a vein pattern, the near-infrared light emission source 105 emits near-infrared light having a wavelength of about 600 nm to 1300 nm or, preferably, about 700 nm to 900 nm.

If the wavelength of the near-infrared light emitted by the near-infrared light emission source 105 is less than 600 nm or more than 1300 nm, the percentage of light that is absorbed by hemoglobin in blood decreases, and it becomes difficult to obtain a suitable vein pattern. Also, if the wavelength of the near-infrared light emitted by the near-infrared light emission source 105 is about 700 nm to 900 nm, the near-infrared light is specifically absorbed by both deoxygenated hemoglobin and oxygenated hemoglobin, and it is therefore possible to obtain a suitable vein pattern.

As such a near-infrared light emission source 105, a light emitting diode (LED) may be used, for example. Further, in stead of using a light emitting diode having the above wavelength band, a combination of a light emitting diode capable of emitting light containing the above wavelength band and a filter for optically limiting the band of emitted light may be used. Further, the near-infrared light emission source 105 may be combined with an optical quantity adjustment filter that adjusts the distribution of light emitted by the light source.

For this near-infrared light emission source 105, emission timing of the near-infrared light and the intensity of the emitted near-infrared light and the like are controlled by the later-described drive control unit 121.

The imaging element 109 has an imaging surface with a plurality of pixels 111 arranged in a lattice structure, and generates vein image data with near-infrared light based on vein transmitted light focused by the microlens array 101. As the imaging element 109 according to the present embodiment can be used, for example, a CCD-image sensor, a CMOS-image sensor, a Thin Film Transistor (TFT)-image sensor, and the like. The imaging element 109 outputs the generated vein image data. Further, the imaging element 109 may record the generated vein image data in the later-described storage unit 139.

Besides, in the vein imaging apparatus 10 according to the present embodiment, the plurality of pixels 111 are assigned to one light-receiving lens of the microlens array 101 as described later. Therefore, in the vein imaging apparatus 10 according to the present embodiment, the near-infrared light (vein transmitted light) condensed by the one light-receiving lens is imaged with the plurality of pixels 111.

The Pixel scanning timing and the like of this imaging element 109 are controlled by the later-described drive control unit 121.

The drive control unit 121 can be realized by, for example, a CPU (Central Processing Unit), a ROM (Read Only Memory), a RAM (Random Access Memory), and the like. The drive control unit 121 performs drive control of the near-infrared light emission source 105 and the imaging element 109. Also, the drive control unit 121 adjusts the driving control of the near-infrared light emission source 105 and the imaging element 109 based on information related to the amount of positional displacement transmitted from the later-described positional displacement amount estimation unit 129. More specifically, the drive control unit 121 performs driving control based on a predetermined synchronization signal and the like. for example, the drive control unit 121 controls from which pixels 111 the information is obtained, and controls the scanning timing of the pixels 111 constituting the imaging element 109. The drive control unit 121 performs drive control related to the emission timing and the emission intensity of the near-infrared light also to the near-infrared light emission source 105.

More specifically, regarding the control of the imaging element 109, the drive control unit 121 performs drive control along a certain direction of the imaging element 109 as such drive control of the imaging element 109 in which pixels along the certain direction are controlled in units of the number of pixels. In other words, on a cutaway view taken along a certain direction of the imaging element 109 according to the present embodiment, the imaging element 109 is considered to include, for example, seven pixels. In this case, the drive control unit 121 performs the driving control by dividing the pixels into seven groups in a direction along this cutting-plane line.

In controlling the near-infrared light emission source 105 and the imaging element 109, the drive control unit 121 can reference various parameters and databases recorded in the later-described storage unit 139.

[Example of Structure of Imaging Unit]

Next, an example of a structure of the imaging unit according to the present embodiment will be described in detail with reference to FIG. 2 to FIG. 6C.

The microlens array 101 of the vein imaging apparatus 10 according to the present embodiment includes, for example, the plurality of microlenses 103, i.e., light-receiving lens as shown in FIG. 2, and the microlenses 103 are arranged in a lattice-pattern on a predetermined board. Each microlens 103 guides vein transmitted light that entered the microlens 103 through a incidence plane to the imaging element 109 (specifically, the pixels 111 of the imaging element 109), which is described later, as shown in FIG. 3, for example. The microlens array 101 is a lens array with a small curvature of field and with no distortion in the depth direction, and therefore suitable image data can be obtained by using such a microlens array 101. The focal position of each microlens 103 constituting the microlens array 101 is set at the position of a vein layer where a vein V exists, which is an imaging target of the vein imaging apparatus 10.

Human skin is known to have a three-layer structure including an epidermis layer, a dermis layer and a subcutaneous tissue layer, and the above-described vein layer exists in the dermis layer. The dermis layer is located at about 0.1 mm to 0.3 mm below the finger surface and has a thickness of about 2 mm to 3 mm. Thus, by setting the focal position of the microlens 103 at the position where the dermis layer exists (e.g. at the position that is about 1.5 mm to 2.0 mm below the finger surface), it is becomes possible to efficiently condense the light transmitted through the vein layer.

Besides, the number of the microlenses 103 disposed in the microlens array 101 according to the embodiment is not limited to the example shown in FIG. 2. The number of the microlenses 103 disposed in the microlens array 101 according to the embodiment may be set freely according to the size of a living body to be imaged, the size of the imaging element 109 or the like.

A plurality of light emitting diodes, which are an example of the near-infrared light emission source 105, are arranged at the opposed ends of the microlens array 101 as shown in FIG. 2, for example. The ends at which the light emitting diodes are arranged preferably correspond to the upper end and the lower end of a part of a living body (which is a finger FG in the example shown in FIGS. 2 and 3). By arranging the light emitting diodes in this manner, it is becomes possible to emit the near-infrared light from the upward and downward direction of the finger FG.

Besides, the number of the near-infrared light emission sources 105 according to the embodiment is not limited to the example shown in FIG. 2, and it may be set freely according to the size of the microlens array 101, an emission area of the near-infrared light emission sources 105 or the like.

Further, a directivity control plate 107 is placed between the microlens array 101 and the near-infrared light emission source 105 as shown in FIGS. 2 and 3, for example. This directivity control plate 107 controls the directivity of direct light 12 that is emitted from the near-infrared light emission sources 105 in such a way that the direct light 12 does not directly enter the microlenses 103 of the microlens array 101.

The near-infrared light that is emitted from the near-infrared light emission sources 105 propagates upward to the surface of the finger FG and enters the finger FG as the direct light 12 as shown in FIG. 3, for example. Because a human body is a suitable scatterer of near-infrared light, the direct light 12 that entered the finger FG propagates while scattering in all directions. A part of such scattered light travels as rear scattering light 13 through the above-described vein layer from the backside to the finger surface, and passes through the vein V on its way. The vein transmitted light that passed through the vein enters the respective microlenses 103 constituting the microlens array 101.

Here, the directivity control plate 107 is placed at the boundary between the adjacent microlenses 103. This directivity control plate 107 makes it possible to control of the directivity of the vein transmitted light, and the light that entered each microlens 103 can be separated from the adjacent microlenses 103. Accordingly, in the vein imaging apparatus 10 according to the embodiment, it becomes possible to select the vein transmitted light to be condensed on the imaging element 109 (specifically, the pixel 111).

[Regarding Image Obtained by Microlens Array]

Figure 4A:
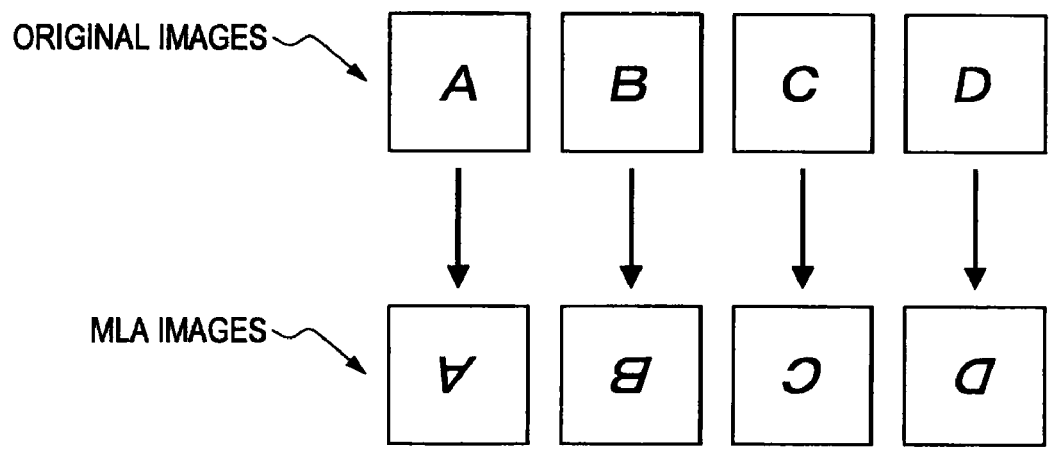
FIG. 4A is an explanatory diagram for illustrating an image taken by a microlens array.
Figure 4B:
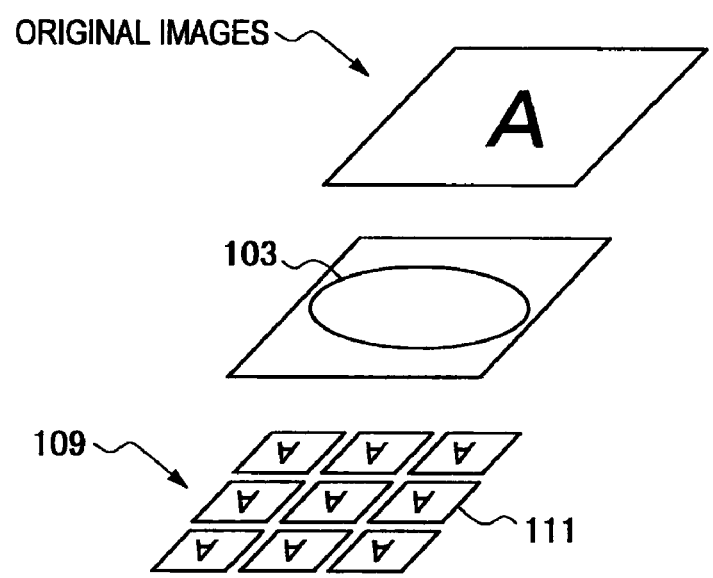
FIG. 4B is an explanatory diagram for illustrating an image taken by a microlens array.

Next, the feature of the images obtained by the microlens array will be described in detail with reference to FIG. 4A and FIG. 4B. FIG. 4A and FIG. 4B are explanatory diagram for illustrating images taken by the microlens array.

Generally, if a certain image is taken by using a microlens array, a taken image is such a image whose up and down side and left and right side are respectively reversed from an original image as shown in FIG. 4A, for example. Further, because a plurality of pixels 111 are assigned to one light-receiving lens (microlens 103), an image whose up and down side and left and right side are reversed is created for all the pixels 111 that are assigned to one microlens 103. For example, if nine (3×3) pixels 111 are assigned to one microlens 103 as shown in FIG. 4B, an image whose up and down side and left and right side are reversed is created for each of the nine pixels 111.

As described later, the vein imaging apparatus 10 according to the present embodiment performs interpolation processing of images using image data generated by each of the plurality of pixels 111 corresponding to one of the microlenses 103.

[Regarding Imaging Element]

Next, the imaging element 109 of the vein imaging apparatus 10 according to the present embodiment will be described in detail with reference to FIG. 5A to FIG. 6C. FIG. 5A, FIG. 5B, FIG. 6A to FIG. 6C are explanatory diagrams for illustrating the imaging element according to the present embodiment.

Figure 5A:
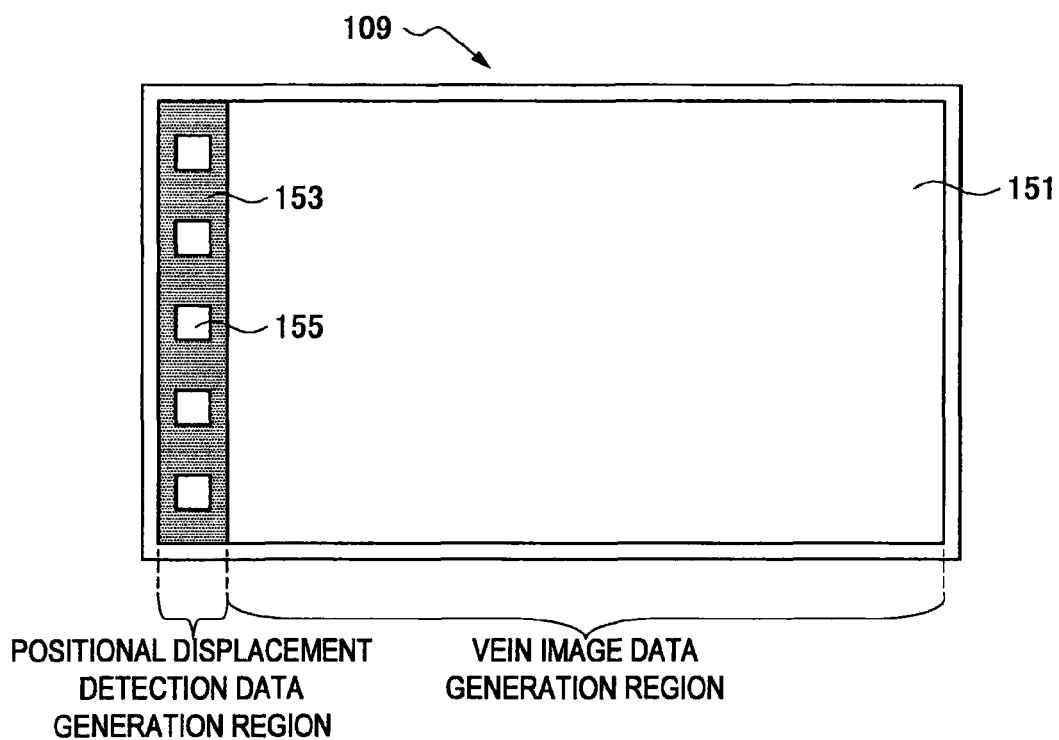
FIG. 5A is an explanatory diagram for illustrating an imaging element according to the embodiment.

In the imaging element 109 of the vein imaging apparatus 10 according to the present embodiment, a region formed with the pixels 111 in the imaging element 109 is divided into, for example, two regions 151 and 153 as shown in FIG. 5A.

The one region 151 is a vein image data generation region used to generate vein image data. The other region 153 is a positional displacement detection data generation region for generating positional displacement detection data used to detect positional displacement occurred due to thermal expansion caused by an environmental temperature and the like.

In the vein image data generation region 151 a plurality of pixels (not shown) is arranged in an array, and the vein transmitted light condensed by the plurality of microlenses 103 of the microlens array 101 reaches the pixels 111. The vein image data output by the vein image data generation region 151 are data related to the intensity of the light detected by the pixels that generated the image data.

In the positional displacement detection data generation region 153 is a plurality of pixels (not shown) arranged in an array. Further, the positional displacement detection data generation region 153 is shielded by a shielding film from the light, for example, as shown in FIG. 5A. Opening sections 155 without the shielding film are arranged in some areas of the positional displacement detection data generation region 153. The number of the opening sections 155 arranged on the positional displacement detection data generation region 153 is not limited to the number of the opening sections 155 shown in the figure, and can be set to any number according to, e.g., a desired degree of accuracy of positional displacement detection result or the size of the imaging element 109. The size of the positional displacement detection data generation region 153 arranged on the imaging element 109 can be determined according to, e.g., the size of the microlens array 101 used together with the imaging element 109.

The positional displacement detection data generation region 153 itself is shielded from external light by means of any method, and light emitted by an illumination light source enters into the opening sections 155. There occurs a displacement of the position of the pixel at which the light emitted from the illumination light source, after passing through the opening section 155, is focused because of, e.g., thermal expansion caused by variation in the environmental temperature and individual differences generated when the apparatus itself is manufactured. Then, the vein imaging apparatus 10 can know the size and the direction of the positional displacement by determining which pixel in the region 153 has detected a pixel signal representing the light entered from the opening section 155.

Figure 5B:
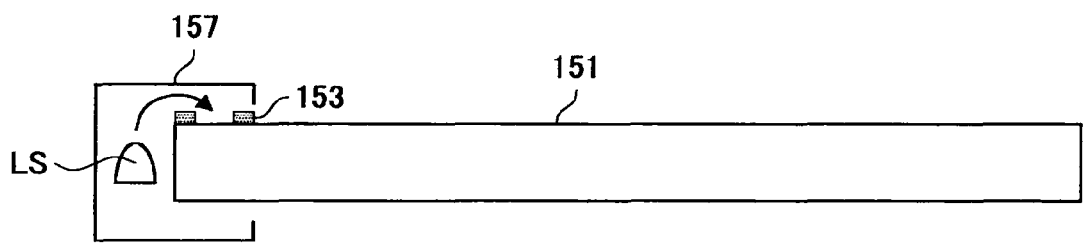
FIG. 5B is an explanatory diagram for illustrating an imaging element according to the embodiment.

FIG. 5B shows an exemplary side view showing the positional displacement detection data generation region 153. As shown in FIG. 5B, the positional displacement detection data generation region 153 is shielded from the external light by a shielding member 157, so that the external light does not enter the positional displacement detection data generation region 153. An illumination light source LS for detecting positional displacement is arranged inside of the shielding member 157. Besides, the illumination light source LS for detecting positional displacement may be a light source arranged solely for detecting positional displacement, or may be a common light source that serves not only for detecting positional displacement but also for taking the vein image.

The light emitted from the illumination light source LS is detected by the pixels via the opening section 155. At this occasion, the positional displacement detection data generation region 153 is shielded from the external light by the shielding member 157, and therefore, the light detected by the positional displacement detection data generation region 153 is emitted from the illumination light source LS.

The example shown in FIG. 5B is merely an example of the positional displacement detection data generation region 153. It should be noted that the configuration of the positional displacement detection data generation region 153 according to the present embodiment is not limited to what is shown in FIG. 5B.

Figure 6A:
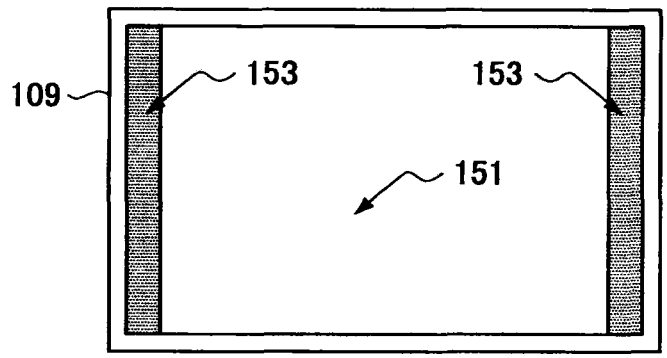
FIG. 6A is an explanatory diagram for illustrating an imaging element according to the embodiment.
Figure 6B:
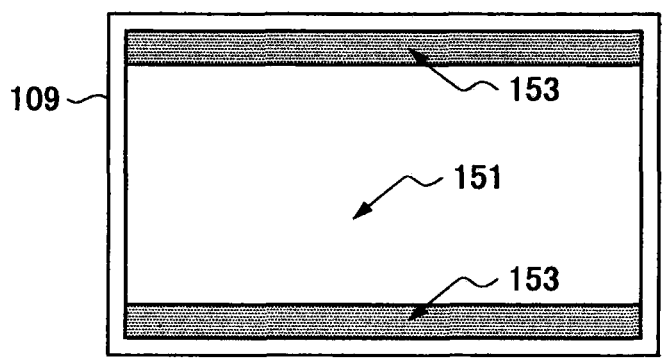
FIG. 6B is an explanatory diagram for illustrating an imaging element according to the embodiment.
Figure 6C:
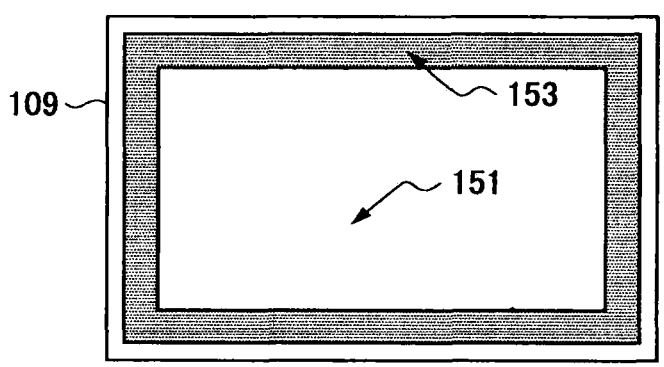
FIG. 6C is an explanatory diagram for illustrating an imaging element according to the embodiment.

For example, such positional displacement detection data generation region 153 may be arranged at one end of the imaging element 109 along one side of the imaging element 109 as shown in FIG. 5A. Alternatively, the positional displacement detection data generation region 153 may be arranged along opposing sides of the imaging element 109 as shown in FIG. 6A and FIG. 6B, or may be arranged along four sides of the imaging element 109 as shown in FIG. 6C. The opening section 155 are omitted in FIG. 6A to FIG. 6C.

[Regarding Configuration of Image Processing Unit]

Next, FIG. 1 is referenced again. The configuration of the image processing unit of the vein imaging apparatus 10 according to the present embodiment will be described in detail.

Figure 7:
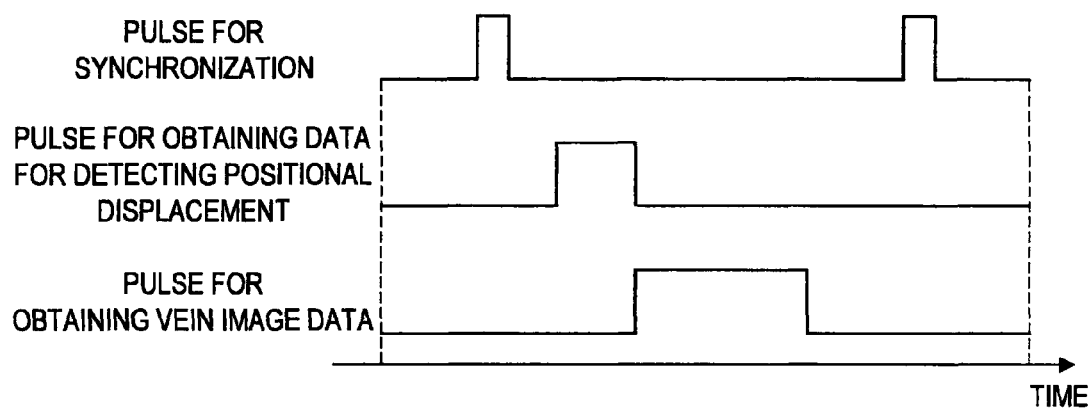
FIG. 7 is an explanatory diagram for illustrating an imaging element according to the embodiment.

The pixel data dividing unit 123 is realized by, for example, CPU, ROM, and RAM. As shown in FIG. 7, for example, the pixel data dividing unit 123 determines, based on pulses for scanning the imaging element 109 input from the drive control unit 121, which of the two regions of the imaging element 109 has output the pixel data transmitted from the imaging element 109. As the example in FIG. 7 shows, the pixel data dividing unit 123 uses three kinds of pulses, namely, a pulse for synchronization in a vertical (or horizontal) direction of the imaging element, a pulse for obtaining data for detecting positional displacement, and a pulse for obtaining vein image data, in order to obtain outputs from the two regions of the imaging element 109. Therefore, the pixel data dividing unit 123 can determine, based on these pulses, whether the data for detecting positional displacement are transmitted or the vein image data are transmitted.

The pixel data dividing unit 123 transmits to the later-described image focus position detection unit 125 the data obtained during a period in which the pulse for obtaining data for detecting positional displacement (namely, data for detecting positional displacement) is in the Hi state. The pixel data dividing unit 123 transmits to the later-described pixel selection unit 131 the data obtained during a period in which the pulse for obtaining vein image data (namely, vein image data) is in the Hi state.

The image focus position detection unit 125 is realized by, for example, CPU, ROM, RAM and the like. The image focus position detection unit 125 references the data for detecting positional displacement transmitted from the pixel data dividing unit 123, and detects which pixel of the positional displacement detection data generation region 153 has detected the light entered from the opening sections 155 arranged in the positional displacement detection data generation region 153. The image focus position detection unit 125 can determine the image focus position of the light entered from the opening section 155 by determining in which part of the positional displacement detection data generation region 153 the pixel having detected the light entered from the opening section 155 is located.

Alternatively, the image focus position detection unit 125 may also determine the image focus position of the light entered from the opening section 155 by detecting a region in which the total light quantity of the light detected by the positional displacement detection data generation region 153 is the largest, instead of identifying the pixel that has detected the light. For example, the image focus position detection unit 125 sets the size of the region of the imaging element corresponding to the opening section 155 as a base unit in considering the total light quantity, and searches per this base unit the data for detecting positional displacement transmitted from the positional displacement detection data generation region 153. The image focus position detection unit 125 can determine, as the image focus position of the light, a part of the region 153 at which the total light quantity is the largest.

The image focus position detection unit 125 transmits information about the image focus position related to the determined light (hereinafter referred to as "image focus position information") to the later-described positional displacement amount estimation unit 127.

The positional displacement amount estimation unit 127 is realized by, for example, CPU, ROM, RAM and the like. The positional displacement amount estimation unit 127 estimates based on the image focus position information transmitted from the image focus position detection unit 125, the size and the direction of positional displacement occurring in the vein imaging apparatus 10. The vein imaging apparatus 10 may have positional displacement between the microlens array and the imaging element (more specifically, displacement in the positional relationship between the MLA, the directivity control plate, and the imaging element) due to, e.g., thermal expansion caused by an environmental temperature when the vein is imaged and assembly error arising when the apparatus is assembled. The positional displacement amount estimation unit 127 can estimate the size and the direction of the positional displacement by identifying how much and in what direction the image focus position represented by the transferred image focus position information is displaced with respect to an original image focus position without the above-described positional displacement. The positional displacement amount estimation unit 127 transmits the information representing the size and the direction of positional displacement (hereinafter, referred to as positional displacement information) to the warning unit 129, the pixel selection unit 131, and the vein image interpolation unit 133, which will be described later.

The warning unit 129 is realized by, for example, CPU, ROM, RAM and the like. The warning unit 129 references the positional displacement information transmitted from the positional displacement amount estimation unit 127. When the positional displacement occurring in the vein imaging apparatus 10 is equal to or more than a predetermined threshold value, the warning unit 129 determines that it is difficult to perform normal vein imaging processing (furthermore, the vein authentication processing) and outputs a warning.

Further, when the warning unit 129 receives, from the later-described authentication unit 137, information indicating that authentication of a vein pattern obtained from a certain user has failed for a predetermined number of times or more, the warning unit 129 may determine that the apparatus itself is under an environment that does not allow the apparatus to perform normal operation, and may output a warning accordingly.

Still further, when the warning unit 129 determines that a positional displacement has occurred to such an extent that it is impossible for the apparatus to perform a normal vein imaging processing (furthermore, the vein authentication processing), the warning unit 129 may stop the vein imaging processing and the vein authentication processing being carried out by the apparatus itself.

Figure 8A:
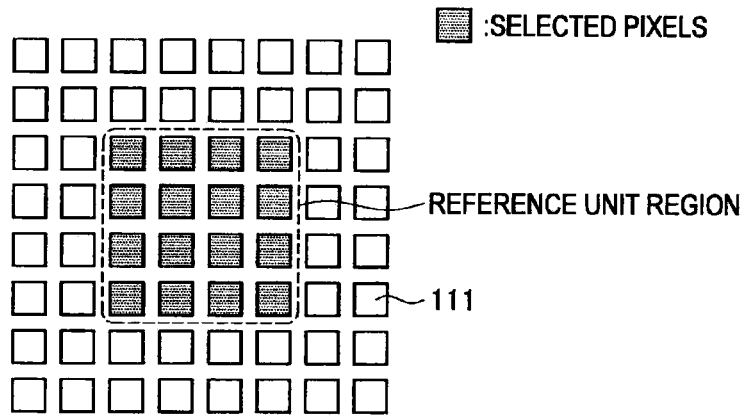
FIG. 8A is an explanatory diagram for illustrating a pixel selection unit according to the embodiment.
Figure 8B:
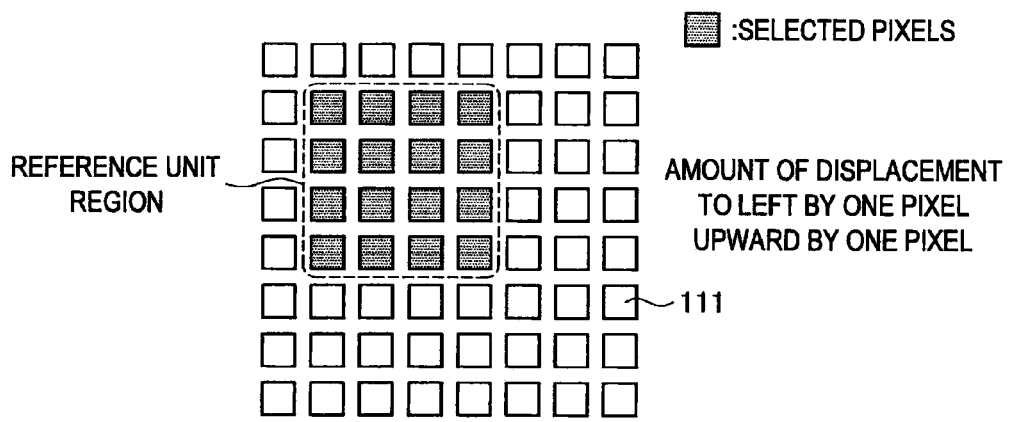
FIG. 8B is an explanatory diagram for illustrating a pixel selection unit according to the embodiment.
Figure 8C:
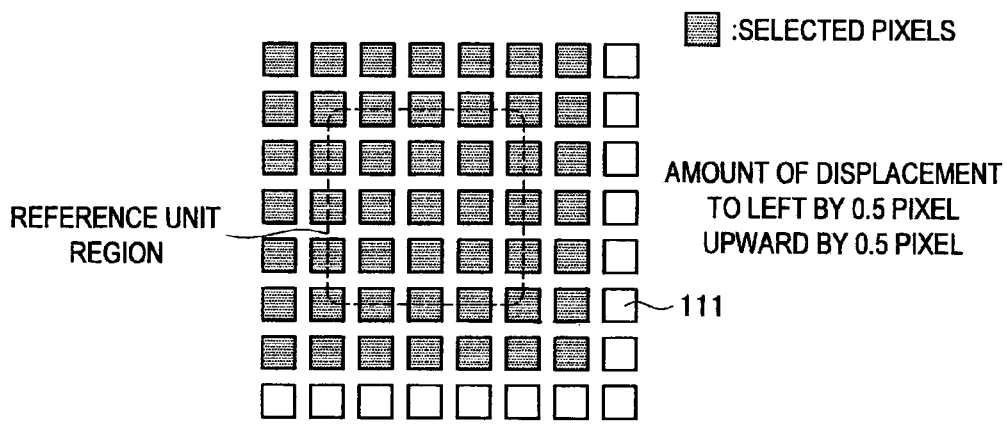
FIG. 8C is an explanatory diagram for illustrating a pixel selection unit according to the embodiment.

The pixel selection unit 131 is realized by, for example, CPU, ROM, RAM and the like. The pixel selection unit 131 selects based on the positional displacement information transmitted from the positional displacement amount estimation unit 127, a pixel for generating vein image data used to generate vein image from among the plurality of pixels 111 corresponding to one of the microlenses 103. Further, the pixel selection unit 131 may select a pixel included in a region in which the total light quantity of the light is the largest from among the plurality of pixels 111 corresponding to one of the microlenses 103 based on the positional displacement information transmitted from the positional displacement amount estimation unit 127. A pixel selection processing performed by the pixel selection unit 131 will be hereinafter described in detail with reference to FIG. 8A to FIG. 8C. FIG. 8A to FIG. 8C are explanatory diagrams for illustrating the pixel selection processing performed by the pixel selection unit 131.

FIG. 8A to FIG. 8C show a case where one microlenses 103 in the microlens array 101 corresponds to 8×8=64 pixels 111 and where the microlens 103 is a lens for reducing the size of the object by one half. In this case, the size of the object is reduced to one half the size. Accordingly, if there is no positional displacement, image data of the object can be obtained by using 4×4=16 pixels located in the central portion from among 64 pixels. Even in this case, the light from the object focuses on pixels other than pixels in the central portion, and the image data obtained from the portion other than the 4×4 pixels in the central portion can also be used to generate an object image.

FIG. 8A shows a case where there is no positional displacement occurring in the vein imaging apparatus 10. A reference unit region serving as a reference unit for pixel selection is a region including 4×4=16 pixels based on, e.g., a magnification of the microlenses 103. As shown in FIG. 8A, when there is no positional displacement, the pixel selection unit 131 selects 4×4 pixels located in the central portion from among 8×8 pixels corresponding to one of the microlenses 103.

FIG. 8B shows a case where the positional displacement is integral multiples of the pixel (namely, there occurs a displacement equivalent to integral multiples of the pixel, such as 1 pixel, 2 pixels, 3 pixels, . . . ). In this case, the pixel selection unit 131 selects 4×4=16 pixels included in the reference unit region by shifting the pixels from which the vein image data are obtained by the amount of occurring positional displacement (namely, equivalent to integral multiples of the pixel). In the example shown in FIG. 8B, the amount of positional displacement includes one pixel in the left direction and one pixel in the upward direction compared with FIG. 8A, and accordingly the pixel selection unit 131 selects 16 pixels included in the reference unit region displaced to left by one pixel and upward by one pixel.

FIG. 8C shows a case where the positional displacement is not integral multiples of the pixel (namely, there occurs a displacement equivalent to real number multiples, such as 0.5 pixel, 1.3 pixels, . . . ). In this case, as shown in FIG. 8C, in addition to 3×3=9 pixels included in the reference unit region, there are pixels of which parts are included in the reference unit region. In this state, information that should be originally taken by only one pixel is extending over two or more pixels, and a so-called crosstalk occurs. In this state, the image quality deteriorates, and the spatial frequency of the image decreases, so that it is difficult for the apparatus to recognize a thin vein as a vein. In this case, as shown in FIG. 8C, the pixel selection unit 131 selects not only the pixels included in the reference unit region but also pixels, detecting light, located around the pixels included in the reference unit region.

The pixel selection unit 131 transmits, to the later-described vein image interpolation unit 133, the information about the thus selected pixels (for example, information for identifying the selected pixels) and the vein image data obtained from the selected pixels.

The vein image interpolation unit 133 is realized by, for example, CPU, ROM, RAM and the like. The vein image interpolation unit 133 generates the vein image based on the vein image data transmitted from the pixel selection unit 131. Further, the vein image interpolation unit 133 performs interpolation processing on the generated vein image based on the positional displacement information transmitted from the positional displacement amount estimation unit 127.

Examples of the interpolation processing performed by the vein image interpolation unit 133 include denoising processing of the generated vein image. The vein image interpolation unit 133 may also perform processing for improving the image quality of the vein image by integrating a plurality of frame images according to the amount of positional displacement transmitted from the positional displacement amount estimation unit 127. When the plurality of frame images are integrated, it takes more time to perform the processing, and the user of the vein imaging apparatus 10 has to wait for a longer time. However, it is possible to curb the occurrence of the situation where a vein may not be imaged due to an environmental temperature and the like (furthermore, the vein authentication processing may not be carried out).

The amount of positional displacement transmitted from the positional displacement amount estimation unit 127 is not integral multiples of the pixel (real number multiples of the pixel), the vein image interpolation unit 133 performs the following interpolation processing using, for example, multi-tap interpolation filter. In other words, as shown in FIG. 8C, the vein image interpolation unit 133 performs interpolation processing (composition processing) of the vein image by using not only the image data obtained from the pixels included in the reference unit region but also the image data, obtained from the pixels that are located around the pixels included in the reference unit region and are detecting light. Even when the amount of positional displacement caused by thermal expansion is not integral multiples of the pixel and the image quality is deteriorating, this processing makes it possible to improve the image quality of the vein image. The interpolation processing of the image using the neighboring pixels may be performed not only when the amount of positional displacement is not integral multiples of the pixel but also when the amount of positional displacement is integral multiples of the pixel.

The vein image interpolation unit 133 transmits, to the later-described vein pattern extraction unit 135, the vein image on which the interpolation processing was performed.
[Regarding Configuration of Authentication Processing Unit]

The vein pattern extraction unit 135 is realized by, for example, CPU, ROM, RAM and the like. The vein pattern extraction unit 135 has, for example, a function of performing preprocessing of the vein pattern extraction on the vein image transmitted from the vein image interpolation unit 133, a function of extracting the vein pattern, and a function of performing a postprocessing of the vein pattern extraction.

Examples of the above preprocessing of the vein pattern extraction include a processing of detecting an outline of a finger from the vein image and recognizing at which position of the vein image the finger is located, and a processing of rotating the taken image using the detected outline of the finger and correcting the angle of the taken image.

The above extraction of the vein pattern is performed by applying a differential filter to the taken image on which the outline detection processing and the angle correction processing are completed. The differential filter is a filter that outputs a large value as an output value at a part where a difference between a pixel of interest and a neighboring pixel is large. In other words, the differential filter is a filter that enhances a line or an edge in an image by the operation using a difference in gradation value between a pixel of interest and pixels in its neighborhood.

Generally, if filtering is performed using a filter h(x, y) on image data u(x, y) with a lattice point (x, y) on a two-dimensional plane as a variable, image data v(x, y) is generated as represented by the following Expression 1. In Expression 1, "*" indicates convolution integral.

$$v(x, y) = u(x, y) * h(x, y) \qquad \text{Expression 1}$$
$$= \sum_{m_1} \sum_{m_2} h(m_1, m_2) u(x - m_1, y - m_2)$$
$$= \sum_{m_1} \sum_{m_2} u(m_1, m_2) h(x - m_1, y - m_2)$$

In the extraction of a vein pattern according to this embodiment, a differentiation filter such as a primary space differentiation filter or a secondary space differentiation filter may be used as the above-described differential filter. The primary space differentiation filter is a filter that calculates a difference in gradation value between a pixel of interest and an adjacent pixel in the horizontal direction and the vertical direction, and a secondary space differentiation filter is a filter that extracts, for a pixel of interest, a part where the amount of change in difference in gradation value is large.

As the secondary space differentiation filter, the following Laplacian of Gaussian (LOG) filter may be used. The LOG filter (Expression 3) is represented by a second order derivative of a Gaussian filter (Expression 2), which is a smoothing filter using the Gaussian function. In the following Expression 2, σ indicates a standard deviation of the Gaussian function, which is a variable indicating the degree of smoothing of the Gaussian filter. Further, σ in the following Expression 3 is a parameter indicating a standard deviation of the Gaussian function as in Expression 2, and an output value when performing LOG filtering can be changed by changing a value of σ.

$$h_{gauss}(x, y) = \frac{1}{2\pi\sigma^2} \exp\left\{-\frac{(x^2 + y^2)}{2\sigma^2}\right\} \qquad \text{Expression 2}$$

$$h_{Log}(x, y) = \nabla^2 \cdot h_{gauss}(x, y) \qquad \text{Expression 3}$$
$$= \left(\frac{\partial^2}{\partial x^2} + \frac{\partial^2}{\partial y^2}\right) h_{gauss}$$
$$= \frac{(x^2 + y^2 - 2\sigma^2)}{2\pi\sigma^6} \exp\left\{-\frac{(x^2 + y^2)}{2\sigma^2}\right\}$$

Examples of the above postprocessing of the vein pattern extraction include threshold processing performed on the taken image to which the differential filter was applied, binarization processing, and thinning processing. After the above postprocessing, a skeleton of the vein pattern can be extracted.

The vein pattern extraction unit 135 transmits the vein pattern and the skeleton thus extracted to the later-described authentication unit 137. In addition, the vein pattern extraction unit 135 may store the extracted vein pattern and the skeleton in the later-described storage unit 139. The vein pattern extraction unit 135 may further store a parameter generated when performing each processing, the progress of processing or the like in the storage unit 139.

The authentication unit 137 is realized by, for example, CPU, ROM, RAM and the like. The authentication unit 137 authenticates the vein pattern by collating the vein pattern generated by the vein pattern extraction unit 135 with an already-registered template.

The vein pattern authentication unit 137 authenticates the generated vein pattern based on the vein pattern that is generated by the vein pattern extraction unit 135 and the template of the vein pattern that has been registered. The vein pattern authentication unit 137 requests the storage unit 139, which is described later, to disclose the registered vein pattern and compares the acquired registered vein pattern with the vein pattern transferred from the vein pattern extraction unit 135. The comparison between the registered vein pattern and the transferred vein pattern can be carried out based on a correlation coefficient, which is calculated as follows, for example. In a case where, as a result of the comparison, the registered vein pattern is determined to be similar to the transmitted vein pattern, the authentication unit 137 determines that the authentication of the transmitted vein pattern is successful. When the registered vein pattern is determined not to be similar to the transmitted vein pattern, the authentication unit 137 determines that the authentication has failed.

The correlation coefficient is defined by the following Expression 4, and it is a statistical indicator that indicates a similarity between two data x={xi} and y={yi}, which is a real value from −1 to 1. If the correlation coefficient indicates a value close to 1, it means that the two data are similar, and if the correlation coefficient indicates a value close to 0, it means that the two data are not similar. Further, if the correlation coefficient indicates a value close to −1, it means that the signs of the two data are reversed.

$$r = \frac{\sum_i (x_i - \bar{x})(y_i - \bar{y})}{\sqrt{\sum_i (x_i - \bar{x})^2} \sqrt{\sum_i (y_i - \bar{y})^2}} \qquad \text{Expression 4}$$

$\bar{x}$: Average value of data $x$ $\bar{y}$: Average value of data $y$

Further, the authentication unit 137 may associate the authentication result with an authentication time and the like, and may record the authentication result as an authentication history in the storage unit 139. By generating the above authentication history, it becomes possible to know who requested the vein pattern authentication and when the requester requested the vein pattern authentication, and further who used the vein imaging apparatus 10 and when the user used the vein imaging apparatus 10.

Further, when authentication of a vein pattern obtained from a certain user has failed for a predetermined number of times or more, the authentication unit 137 transmits, to the warning unit 129, a message indicating that the authentication processing has failed for the predetermined number of times or more. By transmitting such information to the warning unit 129, when it is determined that a normal vein authentication processing may not be performed due to thermal expansion caused by an environmental temperature and the like, it is possible to warn the user of the vein imaging apparatus 10 that the authentication might not be normally performed.

The storage unit 139 stores registered vein patterns of the users of the vein imaging apparatus 10 and other data associated with the registered vein patterns. In addition to these data, the storage unit 139 may store the vein image data generated by the imaging unit, the vein image generated by the vein image interpolation unit 133, and vein pattern and the like extracted by the vein pattern extraction unit 135. In addition, in the storage unit 139 may be stored various programs, data, and the like that are needed in the interpolation processing performed by the vein image interpolation unit 133. Further, in addition to these data, the storage unit 139 may store various parameters or progress of processing that are necessary to be stored while the vein imaging apparatus 10 performs certain processing, various kinds of databases or the like. This storage unit 139 can be freely read and written by each processing unit included in the imaging unit, the image processing unit, and the authentication processing unit.
[Regarding Obtaining Data From Particular Pixel]

Figure 9:
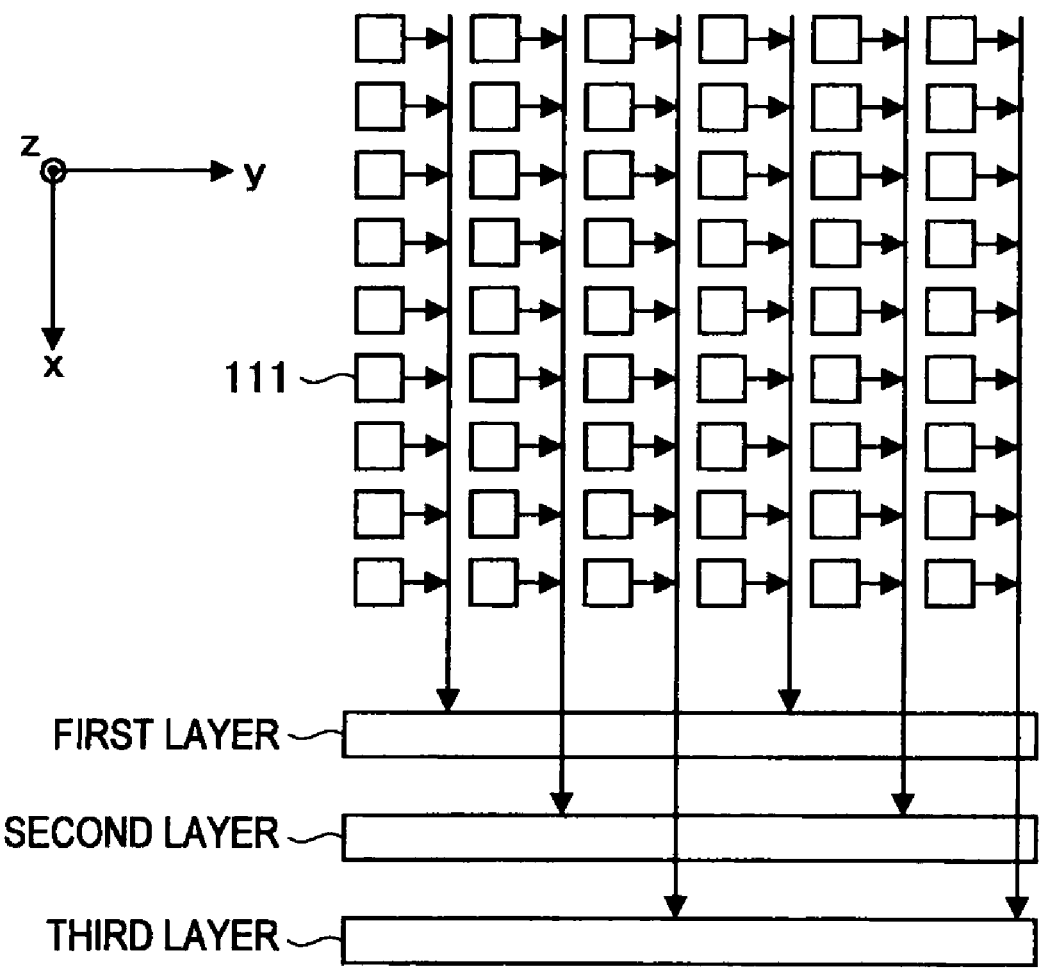
FIG. 9 is an explanatory diagram for illustrating a method for obtaining data from a particular pixel.
Figure 10:
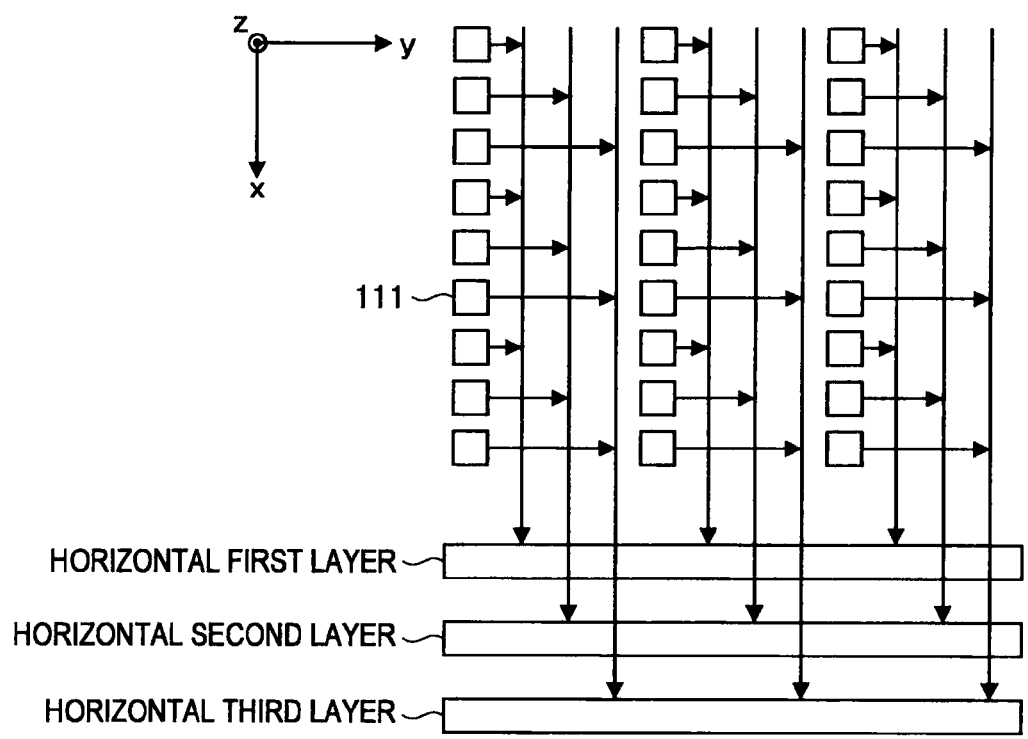
FIG. 10 is an explanatory diagram for illustrating a method for obtaining data from a particular pixel.

A method of obtaining data from a particular pixel will be hereinafter described in detail with reference to FIG. 9 and FIG. 10. FIG. 9 and FIG. 10 are explanatory diagrams for illustrating the method for obtaining data from the particular pixel.

The imaging element 109 of the vein imaging apparatus 10 according to the present embodiment is a multi-layer element. For example, FIG. 9 shows an example of a case where the imaging element 109 is a multi-layer element made of three layers.

In the vein imaging apparatus 10 according to the present embodiment, the imaging element 10 performs line-scanning in a longitudinal direction of a finger, namely, in a direction along y-axis in the figure. Hereinafter, the direction along the y-axis in the figure will be referred to as vertical direction. A direction perpendicular to the vertical direction, namely, a direction along x-axis in the figure will be referred to as horizontal direction.

As shown in FIG. 9, in the vein imaging apparatus 10 according to the present embodiment, image data is output by the drive control unit 121 in units of horizontal lines along a temporal axis of vertical synchronization. In other words, data for some pixels disposed along the horizontal direction is output to the first layer shown in FIG. 9 in synchronization, data for some pixels disposed along the horizontal direction output to the second layer, and data for some pixels disposed along the horizontal direction is output to the third layer. In this manner, according to the control of the drive control unit 121, the imaging element 109 can output with the multiple layers.

Therefore, it becomes possible for the pixel selection unit 131 to transmit information about the pixels to be selected to the drive control unit 121, and for the drive control unit 121 to select an output with a certain layer of the multi-layer element and to select a particular pixel on the horizontal line by the timing control.

In the example shown in FIG. 9, the method for divisionally driving the vertical synchronization line has been described. Alternatively, as shown in FIG. 10, it may also be possible to perform a divisional driving within the horizontal line by means of a circuit.

In the example shown in FIG. 10, there are three types of the pixels 111 on the same horizontal line, i.e., those which output data to the first horizontal layer, those which output data to the second horizontal layer, and those which output data to the third horizontal layer. Therefore, by selecting an output with a certain layer of the multi-layer element and performing timing control for selecting a particular pixel on the vertical line, the drive control unit 121 can select data provided by any pixel.

Alternatively, the divisional driving within the vertical line and the divisional driving within the horizontal line may be used in combination.

An example of the function of the vein imaging apparatus 10 according to the present embodiment has been described in the foregoing. Each of the above-described elements may be constituted using a general-purpose member or circuit, or it may be constituted by the hardware specialized to the function of each element. Further, the function of each element may be entirely realized by a CPU or the like. It is thereby possible to change the configuration to be used as appropriate according to the technique level when implementing the embodiment.

It is possible to develop computer program for realizing each of the functions of the above-described vein imaging apparatus according to the present embodiment and to implement the computer program in a personal computer and the like that can control an imaging apparatus having a microlens array, a near-infrared light emission source, and an imaging element. A computer-readable recording medium in which the above computer program is stored may also be provided. The recording medium may be, for example, a magnetic disk, an optical disk, a magneto-optical disk, and a flash memory. Alternatively, the above computer program may be distributed via, e.g., a network instead of using the recording medium.

The vein imaging apparatus 10 according to the present embodiment may be implemented in an information processing apparatus such as a computer or a server, a mobile terminal such as a cellular phone or a PHS or a portable information terminal (PDA), an automated-teller machine (ATM), an access management apparatus. Further, the vein imaging apparatus 10 according to the present embodiment may be implemented in various kinds of apparatuses such as a game machine, a controller of a game machine or the like.

In the above explanation, the registered vein patterns previously registered as templates are assumed to be recorded in the vein imaging apparatus 10. Alternatively, the registered vein patterns may be stored in a recording medium such as a DVD medium, a Blu-ray medium, a compact flash (registered trademark), a memory stick, or an SD memory card, an IC card or an electronic device equipped with a contactless IC chip or the like, or may be stored in a server that is connected to the vein imaging apparatus 10 via a communication network such as the Internet.

<Regarding Positional Displacement Interpolation Method>

Figure 11:
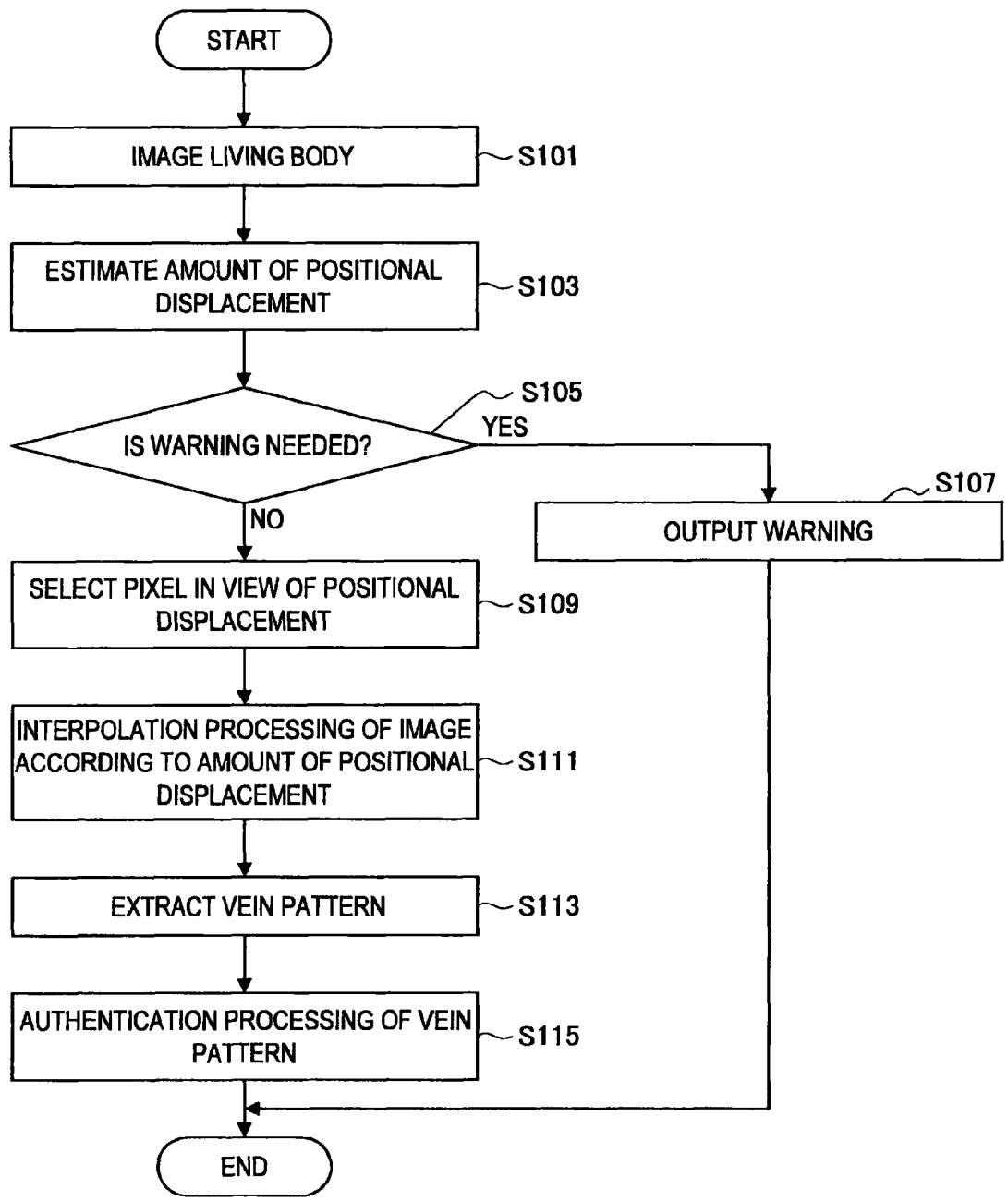
FIG. 11 is a flow diagram for illustrating a positional displacement interpolation method according to the embodiment.

Next, the positional displacement interpolation method according to the present embodiment will be described in detail with reference to FIG. 11. FIG. 11 is a flow diagram for illustrating the positional displacement interpolation method according to the present embodiment.

First, the user of the vein imaging apparatus 10 places a part of the living body such as a finger on the microlens array 101 of the vein imaging apparatus 10. The imaging unit of the vein imaging apparatus 10 performs an imaging processing of the part of the living body placed thereon (step S101).

Further, the image focus position detection unit 125 of the vein imaging apparatus 10 detects the image focus position of the light emitted from the light source used for detecting the positional displacement by using data output from the positional displacement detection data generation region 153 of the imaging element 109. Subsequently, the positional displacement amount estimation unit 127 estimates the size and the direction of the positional displacement occurring in the vein imaging apparatus 10 based on the image focus position information about the image focus position detected by the image focus position detection unit 125 (step S103). The positional displacement amount estimation unit 127 transmits the positional displacement information including the size and the direction of the positional displacement to the warning unit 129, the pixel selection unit 131, and the vein image interpolation unit 133.

The warning unit 129, to which the positional displacement information was transmitted, makes a determination on the amount of positional displacement included in the positional displacement information (step S105), and determines whether the amount of positional displacement exceeds a threshold value at which a warning is required. When the positional displacement occurs according to which a warning is required, the vein imaging apparatus 10 outputs a warning on a display screen (step S107).

When there does not occur the positional displacement according to which a warning is required, the pixel selection unit 131 performs a selection processing of a pixel in view of the positional displacement based on the transmitted positional displacement information (step S109). More specifically, the pixel selection unit 131 selects a pixel outputting image data used for generating the vein image from among the plurality of pixels corresponding to one of the microlenses 103, for each of the microlenses 103 constituting the microlens array 101.

Next, the vein image interpolation unit 133 generates the vein image by using the image data obtained from the pixel selected by the pixel selection unit 131. Next, the vein image interpolation unit 133 performs interpolation processing on the generated vein image according to the amount of positional displacement (step S111). More specifically, the vein image interpolation unit 133 performs integration processing of the plurality of frame images, denoising processing, and interpolation processing of the image using the neighboring pixels.

When the interpolation processing of the image is completed, the vein image interpolation unit 133 transmits the vein image on which the interpolation processing was performed to the vein pattern extraction unit 135. The vein pattern extraction unit 135 extracts the vein pattern from the transmitted vein image (step S113), and transmits the extracted vein pattern to the authentication unit 137.

The authentication unit 137 performs authentication processing of the transmitted vein pattern by using the vein pattern transmitted from the vein pattern extraction unit 135 and the registered vein patterns (templates) stored in the storage unit 139 and the like (step S115).

According to the procedure as described above, it is possible to automatically interpolate the positional displacement due to, e.g., thermal expansion caused by an environmental temperature and assembly error arising when the apparatus is assembled.

In the above explanation, the amount of positional displacement is estimated after the living body is imaged. Alternatively, the vein imaging apparatus 10 may estimate the positional displacement occurring in the apparatus in advance before imaging the living body.

(Second Embodiment)
<Regarding Configuration of Vein Imaging Apparatus>

Figure 12:
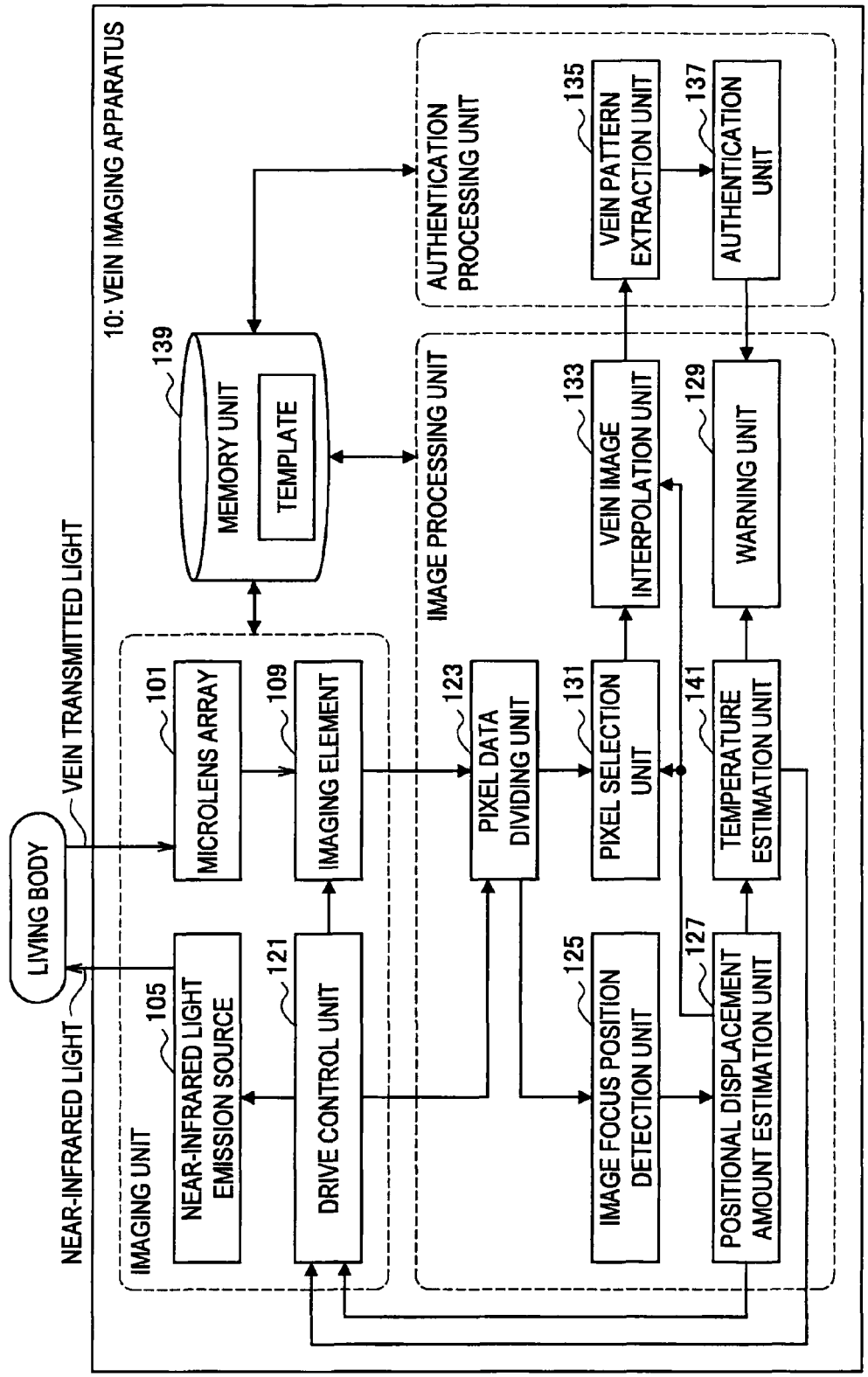
FIG. 12 is a block diagram for illustrating a configuration of a vein imaging apparatus according to a second embodiment of the present invention.

Next, a configuration of a vein imaging apparatus according to the second embodiment of the present invention will be described in detail with reference to FIG. 12. FIG. 12 is a block diagram for illustrating the configuration of the vein imaging apparatus according to the present embodiment.

As shown in FIG. 12, the vein imaging apparatus 10 according to the present embodiment includes, for example, three units, i.e., the imaging unit, the image processing unit, and the authentication processing unit. In this embodiment, the imaging unit and the authentication processing unit according to the present embodiment have the same configuration and achieve almost the same effects as the imaging unit and the authentication processing unit of the vein imaging apparatus 10 according to the first embodiment of the present invention, and accordingly, the detailed description thereof is omitted.

As shown in FIG. 12, the image processing unit mainly includes, for example, the pixel data dividing unit 123, the image focus position detection unit 125, the positional displacement amount estimation unit 127, the warning unit 129, the pixel selection unit 131, the vein image interpolation unit 133, and a temperature estimation unit 141.

In this embodiment, the pixel data dividing unit 123, the image focus position detection unit 125, the pixel selection unit 131, the vein image interpolation unit 133 according to the present embodiment have the same configuration and achieve almost the same effects as each processing unit according to the first embodiment of the present invention, and accordingly, the detailed description thereof is omitted.

Further, the positional displacement amount estimation unit 127 according to the present embodiment has the same configuration and achieve almost the same effects as the positional displacement amount estimation unit 127 according to the first embodiment of the present invention, except that the positional displacement information obtained from the estimation result is not transmitted to the warning unit 129 but is transmitted to the temperature estimation unit 141. Accordingly, the detailed description thereof is omitted.

The temperature estimation unit 141 is realized by, for example, CPU, ROM, RAM and the like. The temperature estimation unit 141 estimates a temperature at which the vein imaging apparatus 10 performed the imaging processing, based on the positional displacement information transmitted from the positional displacement amount estimation unit 127. In this embodiment, the temperature at which the vein imaging apparatus 10 performed the imaging processing may be an external temperature at the location in which the vein imaging apparatus 10 is installed, or may be a temperature that the vein imaging apparatus 10 attains. The temperature estimation unit 141 has a database storing correspondence relationship between the amount of positional displacement occurring in the vein imaging apparatus 10 and the temperature at which the imaging processing is performed, and estimates the temperature from the amount of positional displacement based on this database. This database may relates to, instead of the correspondence relationship between the amount of positional displacement and the temperature, an expansion coefficient calculated from the amount of positional displacement and the temperature at which the imaging processing is performed. The database may express this relationship by an expression representing the correspondence relationship between these two parameters. For example, the above-described data base may be generated by measuring the amount of positional displacement or the expansion coefficient and the like while varying the temperature during the production of the vein imaging apparatus 10.

The temperature estimation unit 141 transmits the temperature obtained from the estimation result to the warning unit 129. Further, the temperature estimation unit 141 may transmit the temperature obtained from the estimation result to the drive control unit 121. Based on information about the temperature transmitted from the temperature estimation unit 141, the drive control unit 121 can control the intensity of the near-infrared light emitted from the near-infrared light emission source 105 and can control the light-receiving time, the frame rate, and the like of the imaging element 109.

Further, the warning unit 129 according to the present embodiment has the same configuration and achieve almost the same effects as the warning unit 129 according to the first embodiment, except that the warning unit 129 gives a warning based on not the positional displacement information transmitted from the positional displacement amount estimation unit 127 but based on the information about the temperature transmitted from the temperature estimation unit 141. Accordingly, the detailed description thereof is omitted.

An example of the functions of the vein imaging apparatus 10 according to the present embodiment has been described in the foregoing. Each of the above-described elements may be constituted using a general-purpose member or circuit, or it may be constituted by hardware specialized to the function of each element. It is thereby possible to change the hardware configuration to be used as appropriate according to the technique level when implementing the embodiment.

Besides, it is possible to make a computer program for implementing each of the functions of the above-described vein imaging apparatus according to the present embodiment, and to implement the computer program in a personal computer and the like that can control an imaging apparatus having a microlens array, a near-infrared light emission source, and an imaging element. A computer-readable recording medium in which the above computer program is stored may also be provided. The recording medium may be, for example, a magnetic disk, an optical disk, a magneto-optical disk, and a flash memory. Alternatively, the above computer program may be distributed via, e.g., a network instead of using the recording medium.

It should be noted that the positional displacement interpolation method performed by the vein imaging apparatus according to the present embodiment has substantially the same flow and achieves almost the same effects as the positional displacement interpolation method performed by the vein imaging apparatus according to the first embodiment of the present invention, and accordingly, the detailed description thereof is omitted.

<Regarding Hardware Configuration>

A hardware configuration of the vein imaging apparatus 10 according to an embodiment of the present invention is described hereinafter with reference to FIG. 13. FIG. 13 is a block diagram for illustrating a hardware configuration of the vein imaging apparatus 10 according to an embodiment of the present invention.

The vein imaging apparatus 10 includes the microlens array 101, the near-infrared light emission source 105, and the imaging element 109. In addition, the vein imaging apparatus 10 includes a CPU 901, a ROM 903, and a RAM 905. Further, the vein imaging apparatus 10 includes a host bus 907, a bridge 909, an external bus 911, an interface 913, an input device 915, an output device 917, a storage device 919, a drive 921, a connection port 923, and a communication device 925.

The CPU 901 functions as a processing unit and a control unit, and it controls the whole or a part of operation in the vein imaging apparatus 10 according to various kinds of programs stored in the ROM 903, the RAM 905, the storage device 919 or a removable recording medium 927. The ROM 903 stores a program to be used by the CPU 901, a processing parameter and the like. The ROM 903 stores a program to be used by the CPU 901, a processing parameter and so on. The RAM 905 primarily stores programs used by the CPU 901 in the execution, parameters and the like that are changed during the execution. The CPU 901, the ROM 903 and the RAM 905 are connected with one another through the host bus 907, which is an internal bus such as a CPU bus.

The host bus 907 is connected to the external bus 911 such as a Peripheral Component Interconnect/Interface (PCI) bus via the bridge 909.

The input device 915 is an operating means to be operated by a user, such as a mouse, a keyboard, a touch panel, buttons, a switch or a lever, for example. For example, the input device 915 may be a remote controlling means (or a remote control) with an infrared ray or another radio wave, or an externally connected device 929 compatible with the operation of the vein imaging apparatus 10, such as a cellular phone or a PDA. Further, the input device 915 includes an input control circuit that generates an input signal based on information input by a user using the above operating means and outputs it to the CPU 901, for example. By operating this input device 915, a user of the vein imaging apparatus 10 can input various kinds of data or give an instruction of a processing operation to the vein imaging apparatus 10.

The output device 917 includes an apparatus capable of visually or audibly notifying obtained information to the user. Examples of such apparatus include a display device such as a CRT display device, a liquid crystal display device, a plasma display device, an EL display device or a lamp, an audio output device such as a speaker or a headphone, or a printer, a cellular phone or a facsimile. The output device 917 outputs, for example, results obtained by various processing by the vein imaging apparatus 10. Specifically, the display device displays, as a text or an image, a result obtained by various processing of the vein imaging apparatus 10. The audio output device converts an audio signal containing reproduced audio data, acoustic data or the like into an analog signal and outputs it.

The storage device 919 is a device for data storage that is configured as an example of a storage unit of the vein imaging apparatus 10. The storage device 919 may include a magnetic storage device such as a hard disk drive (HDD), a semiconductor storage device, an optical storage device, a magneto-optical storage device or the like. This storage device 919 stores a program to be executed by the CPU 901, various data, or various data acquired from the outside, for example.

The drive 921 is a reader/writer for a recording medium, which is built in the vein imaging apparatus 10 or attached thereto. The drive 921 reads information that is recorded in the removable recording medium 927 such as a magnetic disk, an optical disk, a magneto-optical disk or semiconductor memory which is attached thereto and outputs the information to the RAM 905. Further, the drive 921 can write information into the removable recording medium 927 such as a magnetic disk, an optical disk, a magneto-optical disk or semiconductor memory which is attached thereto. Examples of the removable recording medium 927 include a DVD medium, an HD-DVD medium, and a Blu-ray medium. In addition, examples of the removable recording medium 927 include a compact flash (registered trademark) (CF), a memory stick, and a secure digital (SD) memory card. Further, the removable recording medium 927 may be an integrated circuit (IC) card equipped with a contactless IC chip or an electronic appliance.

The connection port 923 is a port for directly connecting devices to the vein imaging apparatus 10. Examples of the connection port 923 include a universal serial bus (USB) port, an IEEE 1394 port such as i.Link, and a small computer system interface (SCSI) port. In addition, examples of the connection port 923 include an RS-232C port, an optical audio terminal, and a high-definition multimedia interface (HDMI) port. By connecting the externally connected device 929 to the connection port 923, the vein imaging apparatus 10 can directly acquire various data from the externally connected device 929 or supply various data to the externally connected device 929.

The communication device 925 is a communication interface that is constituted by a communication device or the like for connecting to a communication network 931, for example. The communication device 925 may be a communication card for wired or wireless local area network (LAN), Bluetooth, or wireless USB (WUSB). Alternatively, the communication device 925 may be a router for optical communication, a router for asymmetric digital subscriber line (ADSL), or a modem for each kind of communication. This communication device 925 can transmit and receive a signal or the like in conformity to a prescribed protocol such as TCP/IP on the Internet or with other communication devices, for example. Further, the communication network 931 that is connected to the communication device 925 includes a wired or wireless network or the like, and it may be the Internet, home LAN, infrared data communication, radio wave communication, satellite communication or the like.

An example of the hardware configuration that can implement the functions of the vein imaging apparatus 10 according to each embodiment of the present invention has been described in the foregoing. Each of the above-described elements may be constituted using a general-purpose member or circuit, or it may be constituted by hardware specialized to the function of each element. It is thereby possible to change the configuration to be used as appropriate according to the technique level when implementing the embodiment.

<Summary>

As hereinabove described, according to each embodiment of the present invention, the neighboring pixels around the imaging region are used to detect the positional displacement between the microlens array and the imaging element, so that the vein imaging apparatus can automate interpolation processing by means of image processing and optimum sampling of the vain imaging apparatus at each temperature.

Depending on the temperature during imaging, thermal expansion may occur in the microlens array included in the vein imaging apparatus. Accordingly, there may arise an issue in deterioration of the image quality and occurrence of the crosstalk, and there may arise an issue that the spatial frequency decreases. However, the vein imaging apparatus according to each embodiment of the present invention estimates the amount of positional displacement based on data obtained from a region arranged on a portion of the imaging element, and performs the interpolation processing of the image based on the positional displacement. As a result, the above-described issues can be solved. Further, according to each embodiment of the present invention, it is also possible to handle not only the positional displacement caused by thermal expansion but also the positional displacement caused by assembly error during production.

It should be understood by those skilled in the art that various modifications, combinations, sub-combinations and alterations may occur depending on design requirements and other factors insofar as they are within the scope of the appended claims or the equivalents thereof.

The present application contains subject matter related to that disclosed in Japanese Priority Patent Application JP 2009-117985 filed in the Japan Patent Office on May 14, 2009, the entire content of which is hereby incorporated by reference.

What is claimed is:

1. A vein imaging apparatus comprising:
    a lens array including a plurality of light-receiving lenses disposed in an array;
    a near-infrared light emission source which is arranged at an end of the lens array and emits a near-infrared light to a part of a living body;
    an imaging element including:
        a vein image data generation region for generating image data of a vein based on the near-infrared light that was condensed by the lens array and that was scattered in the living body and transmitted through the vein; and
        a positional displacement detection data generation region that includes a shielding member configured to prevent external light from entering the positional displacement detection data generation region, an illumination light source arranged inside of the shielding member, a shielded section in which pixels are shielded from the illumination light by a shielding film and an opening section in which pixels are not shielded from the illumination light, and generates data for detecting a positional displacement that is used to detect, based on the illumination light received via the opening section, variation in an image focus position according to an imaging temperature, wherein a plurality of pixels are assigned to one of the light-receiving lenses;
    an image focus position detection unit for detecting a image focus position at imaging temperature based on the data for detecting positional displacement obtained from the positional displacement detection data generation region;
    a positional displacement amount estimation unit for estimating an amount of displacement of the image focus position at the imaging temperature based on the image focus position detected by the image focus position detection unit; and
    a pixel selection unit for selecting based on the amount of displacement, a pixel generating the vein image data used to generate vein image from among the plurality of pixels corresponding to one of the light-receiving lenses.

2. The vein imaging apparatus according to claim 1, further comprising:
    a drive control unit for performing drive control of at least one of the near-infrared light emission source and the imaging element,
    wherein the drive control unit performs drive control of the near-infrared light emission source and/or the imaging element based on the amount of displacement transmitted from the positional displacement amount estimation unit.

3. The vein imaging apparatus according to claim 2, further comprising:
    a vein pattern extraction unit that extracts a vein pattern from the vein image generated using the vein image data; and
    a vein image interpolation unit that performs interpolation processing on the vein image, from which the vein pattern is extracted, based on the amount of displacement estimated by the positional displacement amount estimation unit.

4. The vein imaging apparatus according to claim 3, wherein the vein image interpolation unit performs interpolation processing on the vein image by using the vein image data obtained from the pixels, located around a reference unit region serving as a reference unit for pixel selection by the pixel selection unit, from among the plurality of pixels corresponding to one of the light-receiving lenses.

5. The vein imaging apparatus according to claim 3, further comprising:
    a storage unit for storing data related to the vein image.

6. The vein imaging apparatus according to claim 5, further comprising:
    an authentication processing unit, for performing authentication processing of the vein image generated by the image processing unit.

7. The vein imaging apparatus according to claim 1, wherein the pixel selection unit selects a pixel included in a region in which the sum of the light quantity detected by the pixel is the largest from among the plurality of pixels corresponding to one of the light-receiving lenses.

8. The vein imaging apparatus according to claim 1, further comprising a temperature estimation unit for estimating the imaging temperature based on the amount of displacement obtained from the positional displacement amount estimation unit.

9. The vein imaging apparatus according to claim 8, further comprising:
   a warning unit that gives a warning when the amount of displacement output from the positional displacement amount estimation unit or the imaging temperature output from the temperature estimation unit is equal to or more than a predetermined threshold value.

10. The vein imaging apparatus according to claim 1, further comprising:
    a directivity control plate for controlling the directivity of the light that was scatted by the living body and transmitted through the vein and received by the light-receiving lens,
    wherein, the directivity control plate is placed at the boundary between adjacent light-receiving lenses in the lens array, for separating the light received by the light-receiving lens from the light received by the adjacent light-receiving lens in the lens array.

11. A positional displacement interpolation method comprising the steps of;
    detecting a image focus position at imaging temperature based on data for detecting positional displacement obtained from a positional displacement detection data generation region of a vein imaging apparatus including:
       a lens array including a plurality of light-receiving lenses disposed in an array,
       a near-infrared light emission source which is arranged at an end of he lens array and emits a near-infrared light to a part of a living body, and
       an imaging element including a vein image data generation region for generating image data of a vein based on the near-infrared light that was condensed by the lens array and that was scattered in the living body and transmitted through the vein, and the positional displacement detection data generation region that includes a shielded section in which pixels are shielded from a light and an opening section in which pixels are not shielded from the light, and generates data for detecting a positional displacement that is used to detect, based on the light received via the opening section, variation in an image focus position according to an imaging temperature, wherein a plurality of pixels are assigned to one of the light-receiving lenses;
    estimating an amount of displacement of the image focus position at the imaging temperature based on the detected image focus position; and
    selecting, based on the amount of displacement, a pixel generating the vein image data used to generate vein image from among the plurality of pixels corresponding to one of the light-receiving lenses.

12. The positional displacement interpolation method according to claim 11, wherein the imaging element further comprises:
    a shielding member so that external light does not enter the positional displacement detection data generation region, an illumination light source arranged inside of the shielding member, and the shielded section in which pixels are shielded from the illumination light by a shielding film and the opening section in which pixels are not shielded from the illumination light.

13. The vein imaging method according to claim 11, further comprising:
    determining, based on pulses for scanning input from the imaging element, if data transmitted from the imaging element is generated by the vein image data generation region or the positional displacement detection data generation region.

14. The positional displacement interpolation method according to claim 11, further comprising:
    performing drive control of the near-infrared light emission source and the imaging element,
    wherein performing drive control of at least one of the near-infrared light emission source or the imaging element is based on the amount of displacement transmitted from the displacement of the image focus position.

15. The positional displacement interpolation method according to claim 11, further comprising:
    estimating the imaging temperature based on the estimated amount of displacement of the image focus position.

16. The positional displacement interpolation method according to claim 15, further comprising:
    giving a warning when the estimated amount of displacement or the estimated imaging temperature is equal to or more than a predetermined threshold value.

17. The positional displacement interpolation method of claim 11, wherein:
    the positional displacement detection data generation region includes a shielding member configured to prevent external light from entering the positional displacement detection data generation region, and an illumination light source arranged inside of the shielding member,
    the pixels in the shielded section are shielded from the illumination light by a shielding film and the pixels in the opening section are not shielded from the illumination light, and
    the generated data, for detecting a positional displacement that is used to detect variation in an image focus position according to an imaging temperature, wherein a plurality of pixels are assigned to one of the light-receiving lenses, is based on the illumination light received via the opening section.

18. A non-transitory computer-readable medium storing instructions, which when executed by a processor causes a computer that controls a vein imaging apparatus to realize:
    an image focus position detection function for detecting a image focus position at imaging temperature based on data for detecting positional displacement obtained from a positional displacement detection data generation region;
    a positional displacement amount estimation function for estimating an amount of displacement of the image focus position at the imaging temperature based on the image focus position detected by the image focus position detection function; and
    a pixel selection function for selecting, based on the amount of displacement, a pixel for generating vein image data used to generate vein image from among a plurality of pixels corresponding to one of light-receiving lenses,
    wherein the vein imaging apparatus includes:
       a lens array including a plurality of light-receiving lenses disposed in an array, a near-infrared light emission source which is arranged at an end of the lens array and emits a near-infrared light to a part of a living body, and an imaging element including a vein image data generation region for generating image data of a vein based on the near-infrared light that was condensed by the lens array and that was scattered in the living body and transmitted through the vein, and the positional displacement detection data generation region that includes a shielded section in which pixels are shielded from a light and an opening section in which pixels are not shielded from the light, and generates data for detecting a positional displacement that is used to detect, based on the light received via the opening section, variation in an image focus position according to an imaging temperature, wherein a plurality of pixels are assigned to one of the light-receiving lenses.

19. The non-transitory computer-readable medium according to claim 18, wherein the imaging element further comprises:

a shielding member so that external light does not enter the positional displacement detection data generation region, an illumination light source arranged inside of the shielding member, and the shielded section in which pixels are shielded from the illumination light by a shielding film and the opening section in which pixels are not shielded from the illumination light.

* * * * *